United States Patent [19]
Xu et al.

[11] Patent Number: 5,866,398
[45] Date of Patent: Feb. 2, 1999

[54] METHOD FOR CLONING AND PRODUCING THE BSlI RESTRICTION ENDONUCLEASE IN *E. COLI*

[75] Inventors: Shuang-yong Xu, Lexington; Jian-ping Xiao, Wenham, both of Mass.

[73] Assignee: New England Biolabs, Inc., Beverly, Mass.

[21] Appl. No.: 951,871

[22] Filed: Oct. 17, 1997

[51] Int. Cl.$^6$ ............................................. C12N 9/22
[52] U.S. Cl. ..................... 435/199; 435/193; 435/320.1; 435/252.3; 536/23.2
[58] Field of Search .................... 435/199, 193, 435/320.1, 252.3, 478; 536/23.2

[56] References Cited

U.S. PATENT DOCUMENTS 5,200,333  4/1993  Wilson ................................. 435/172.3
5,498,535  3/1996  Fomerkov et al. ................. 435/172.3

OTHER PUBLICATIONS

Roberts and Macelis, Nucl. Acids Res. 24:223–235 (1996).
Kong, et al., J. Biol. Chem., 268:1965–1975 (1993).
Kosykh, et al., Mol. Gen. Genet., 178:717–719 (1980).
Mann, et al., Gene, 3:97–112 (1978).
Walder, et al., Proc. Natl. Acad. Sci. USA 78:1503–1507 (1981).
Bougueleret, et al., Nucl. Acids. Res., 12:3659–3676 (1984).
Gingeras and Brooks, Proc. Natl. Acad. Sci. USA, 80:402–406 (1983).
Theriault and Roy, Gene, 19:355–359 (1982).
Blumenthal, et al., J. Bacteriol., 164:501–509 (1985).
Kiss, et al., Nucl. Acids Res., 13:6403–6421 (1985).
Szomolanyi, et al., Gene, 10:219–225 (1980).
Janulatis, et al., Gene, 20:197–204 (1982).
Kiss and Baldaud, Gene, 21:111–119 (1983).
Walder, et al., J. Biol. Chem., 258:1235–1241 (1983).
Fomenkov, et al., Nucl. Acids Res., 22:2399–2403 (1994).
Jack, et al., Nucl. Acids Res., 19:1825–1829 (1991).
Stankevicius, et al., 1. p.11 "Unique Structure of the TypeII Restriction–Modification System Bpu101" The 4th New England Biolabs Workshop on Biological DNA Modification Innsbruck, IGLS, Sep. 2, 1997 –Sep. 7, 1997, p. 91.

*Primary Examiner*—Charles L. Patterson, Jr.
*Attorney, Agent, or Firm*—Gregory D. Williams

[57] ABSTRACT

The methylase selection method was used to clone the BslI methylase gene (bslIM) from *Bacillus species*. A partially active BslI methylase lacking the 17 amino acid residues at the N-terminus was cloned in *E. coli* using expression vector pRRS. Inverse PCR was used to clone the missing portion of the BslI methylase. After cloning the complete BslI methylase gene and its upstream DNA sequences, a RadC homolog was found upstream of the BslI methylase. Because methylase gene and restriction endonuclease gene are located in proximity to each other in a particular restriction-modification system, efforts were made to clone the downstream DNA by inverse PCR. After two round of inverse PCR reactions two open reading frames (ORF) were found downstream of the BslI methylase gene. Expression of the first ORF (ORF1) in a T7 expression vector did not yield any active BslI endonuclease. Expression of the second ORF (ORF2) in *E. coli* and assay of the crude cell extract indicated that this gene product has DNA nicking activity. The gene product of ORF2 alone does not constitute BslI endonuclease activity. Expression of ORF1 and ORF2 in the same *E. coli* cell produces BslI endonuclease activity. BslI endonuclease activity can be reconstituted in vitro by mixing gene product of ORF1 and ORF2 together.

7 Claims, 6 Drawing Sheets

FIG. 1A

```
              10                       30                      50
ATGAATTGGATATTTAATACTCTGATTCAATTTCTTGAAGATTTAAATATAGATCCGAGC
 M  N  W  I  F  N  T  L  I  Q  F  L .E  D  L  N  I  D  P  S
              70                       90                     110
GTAGTATCTTTGATTGATGAGGATGCTAAAAAGCTTGAAGAACAATTCCCTAAGGCATTA
 V  V  S  L  I  D  E  D  A  K  K  L  E  E  Q  F  P  K  A  L
             130                      150                     170
AAACATCCAGTTGTAGATGAGGAAATTGTATACAAAATACTTTGTGAAAAGTATAATCTA
 K  H  P  V  V  D  E  E  I  V  Y  K  I  L  C  E  K  Y  N  L
             190                      210                     230
AATGCTTTAAATGTaAAAACAATATCTGAGACTTTAAATAAAGAATATAAATTTGGAAGG
 N  A  L  N  V  K  T  I  S  E  T  L  N  K  E  Y  K  F  G  R
             250                      270                     290
AATTCGAAAACTGCGTTAAAAAAGTATCTTGATTATGGTAAAGAGGAGTATTTGATTCAA
 N  S  K  T  A  L  K  K  Y  L  D  Y  G  K  E  E  Y  L  I  Q
             310                      330                     350
TTTTTTAATACCCTTATGCTAGAAAACaATACATATATAGATaGAGAGTATATTGAAAGT
 F  F  N  T  L  M  L  E  N  N  T  Y  I  D  R  E  Y  I  E  S
             370                      390                     410
GTGCTGGCTTTTTGTGAACCTGTTTCAAAAGAAAAAATTAAAAATGAGTTTaTaAAGCTT
 V  L  A  F  C  E  P  V  S  K  E  K  I  K  N  E  F  I  K  L
             430                      450                     470
TGGAATGAAGCTAATGAAGTTAATGAATACGGTAAGTTAAAGGATTACTTATTGGAATT
 W  N  E  A  N  E  V  N  E  Y  G  K  L  K  D  Y  L  L  G  I
             490                      510                     530
TATTCAAAGCTATTCTCAATGGGACTAGAAAATTTAAGACTAATAGAAATTTATAATTCT
 Y  S  K  L  F  S  M  G  L  E  N  L  R  L  I  E  I  Y  N  S
             550                      570                     590
AATGAAAGCCTTATAAAAAAGGTATTTAAATACGAGTCAACGATAAAGGAGTTAAAGGAG
 N  E  S  L  I  K  K  V  F  K  Y  E  S  T  I  K  E  L  K  E
             610                      630                     650
TACTGCTTATCTAATCAAGAGTCAATTACTGCTGGTTTAGCCATCAAGATGTTTAATGAA
 Y  C  L  S  N  Q  E  S  I  T  A  G  L  A  I  K  M  F  N  E
             670                      690                     710
AAGTATATGGAATTAATGAAAAAAGAATATCAACAAGATGCTATAGCCTTAAAAACTTGAG
 K  Y  M  E  L  M  K  K  E  Y  Q  Q  D  A  I  A  L  K  L  E
             730                      750                     770
GAGCATATGAATCAATTGTATGTTGATAATAATATTAATGAATATCCTTATATTTTTGAC
 E  H  M  N  Q  L  Y  V  D  N  N  I  N  E  Y  P  Y  I  F  D
             790                      810                     830
CGGGGAAATGATATTCTACTCTTACCTACAGAAGAGTATGACTTTGTTTATTTCCATATA
 R  G  N  D  I  L  L  P  T  E  E  Y  D  F  V  Y  F  H  I
             850                      870                     890
GATCAGGATTTTTTTAATAGATTCCAAGATGAAAATAAAATTCTTGGATTATGTACTTTCG
 D  Q  D  F  F  N  R  F  Q  D  E  N  K  F  L  D  Y  V  L  S
             910                      930                     950
TCCATAAAACAAATTTATCGTGTGTTAGCTAATGAAAAAGTTTTTGCGTTGAAGATTGAT
 S  I  K  Q  I  Y  R  V  L  A  N  E  K  V  F  A  L  K  I  D
             970                      990                    1010
AATATTTACAATAATGAAAAAAATTTGAAATGGAACTTTATCCAAAACTAACAATCTAC
 N  I  Y  N  N  E  K  N  L  K  W  E  L  Y  P  K  L  T  I  Y
            1030                     1050                    1070
TCTGAACATTTTATACAAACAAAAGAAACTGCTAGGTTTTATAAAGCATACGATATAGCT
 S  E  H  F  I  Q  T  K  E  T  A  R  F  Y  K  A  Y  D  I  A
            1090                     1110                    1130
AAAGATTTGCTTAGTAAACACGAATTTAGGCTATTAGAGAATGATTCAGAGAAAAATAGA
 K  D  L  L  S  K  H  E  F  R  L  L  E  N  D  S  E  K  N  R
```

FIG. 1B

```
         1150                1170                1190
GAAAATATTTTAAAAGAGTATTTTTCTGGAAAAATAAGTGAAGATGAGTTATTTCTTTA
E   N   I   L   K   E   Y   F   S   G   K   I   S   E   D   E   L   F   S   L
         1210                1230                1250
GTTCATGTAAATATGAAAAAAGAACATTTCTTTGAATTTCTAAACAGATTTAAATATGTA
V   H   V   N   M   K   K   E   H   F   F   E   F   L   N   R   F   K   Y   V
         1270                1290                1310
CATTATGGTTTTACATTTAATGATTGTCTAGTGTTAGACAGGGTTGATAAAAGCTTTGCA
H   Y   G   F   T   F   N   D   C   L   V   L   D   R   V   D   K   S   F   A
         1330                1350                1370
AATGGTGAGCTAGAAAATGTCATAAGTAATGCAACAGAAATACTTCTTATTTTCTATAAG
N   G   E   L   E   N   V   I   S   N   A   T   E   I   L   L   I   F   Y   K
         1390                1410                1430
TTTAGAGCGGATCAAAGGAGAATTCCTTGTCCTTCTTGTGGTAGTTTGAATATTTCTGGG
F   R   A   D   Q   R   R   I   P   C   P   S   C   G   S   L   N   I   S   G
         1450                1470                1490
AACTCTTACCCAGAAATAAATAATAGAAGCTGGGAATGTAAATCTCCTTATTGTCCAGAC
N   S   Y   P   E   I   N   N   R   S   W   E   C   K   S   P   Y   C   P   D
         1510                1530                1550
AGGAGTAAATCTAATCGTGGTAAACGATATTCTAAAAAATCTAATTATATGCAATGGGGA
R   S   K   S   N   R   G   K   R   Y   S   K   K   S   N   Y   M   Q   W   G
         1570                1590                1610
GCTATTTATCCAAAATCTCATGACATCATTCCTCGAGAATTAATTAAAAAGTGGAGAAGA
A   I   Y   P   K   S   H   D   I   I   P   R   E   L   I   K   K   W   R   R
         1630                1650                1670
GATATAATTGTAATTAATAATGAACAAGAAATCTTTGAGATGCTTGTGAAATACTTTAGT
D   I   I   V   I   N   N   E   Q   E   I   F   E   M   L   V   K   Y   F   S
         1690                1710                1730
TTCACAGATGAAAAATTGTTATTTATCAATACGAATGAACTACCTAGTGTAGTTACAGAA
F   T   D   E   K   L   L   F   I   N   T   N   E   L   P   S   V   V   T   E
         1750                1770                1790
CGTGAAAATAGAAAGGTTGTTATATTATCTCAAAAGCTGAAAGAAAAAGCATATACAAGT
R   E   N   R   K   V   V   I   L   S   Q   K   L   K   E   K   A   Y   T   S
         1810                1830                1850
AATGTAGTTGTAAAGGAAAGCTTAGAAGGAGAAATAGAGTTTTTCAAGAACGGTTTATAT
N   V   V   V   K   E   S   L   E   G   E   I   E   F   F   K   N   G   L   Y
         1870                1890                1910
CTCAAGAATTTTACTGAGTTGTATTTACCAGAGGATCAAAGAAGAGTCTCTCCTGAAATA
L   K   N   F   T   E   L   Y   L   P   E   D   Q   R   R   V   S   P   E   I
         1930                1950                1970
AATAACTTTTTAAATAGTGGGGGACGGTTAAAATTAATACAAGGAGATAGTTACGAAGTA
N   N   F   L   N   S   G   G   R   L   K   L   I   Q   G   D   S   Y   E   V
         1990                2010                2030
TTAAAAAGTGTAGAAGATAATACTTTTGCAGCAGCAGTGACTTCGCCTCCATACTACAAT
L   K   S   V   E   D   N   T   F   A   A   A   V   T   S   P   P   Y   Y   N
         2050                2070                2090
GCTAGGGAATATTCTCAATGGCCGAACCTATATTTATACTTTAATGATATGTATAACATT
A   R   E   Y   S   Q   W   P   N   L   Y   L   Y   F   N   D   M   Y   N   I
         2110                2130                2150
ATTAAAGAATGCTTTAGAACTCTAAAACCGGGTAGTGTATTCCTTTATAACATTGCTGAT
I   K   E   C   F   R   T   L   K   P   G   S   V   F   L   Y   N   I   A   D
         2170                2190                2210
ATCGTTGACAATGAAAATATAATAGTCAAATCATCAATGGGAAATAAAAGAATCCCTCTT
I   V   D   N   E   N   I   I   V   K   S   S   M   G   N   K   R   I   P   L
```

FIG. 1C

```
         2230                2250                2270
GGTGCATATACTATTTATTTCTTCCAAAAGGCAGGTTTTGAGCTACTAGATAATATTATA
 G  A  Y  T  I  Y  F  F  Q  K  A  G  F  E  L  L  D  N  I  I
         2290                2310                2330
TGGGATAAAGGCGAGCCACAAAGTAATAGGCAAAAAAATGATGGTAAGTTTACACCTCAC
 W  D  K  G  E  P  Q  S  N  R  Q  K  N  D  G  K  F  T  P  H
         2350                2370                2390
TATCAAAAGCCACTAAATGCTTATGAGCATATGTTTATTTTTAAAAAGACAGGCGCTCCT
 Y  Q  K  P  L  N  A  Y  E  H  M  F  I  F  K  K  T  G  A  P
         2410                2430                2450
TTAACTTTAAGTGACGATTGGCAAAGTAAACGAGGAAGCTGGATTAAAAATATAGTACCT
 L  T  L  S  D  D  W  Q  S  K  R  G  S  W  I  K  N  I  V  P
         2470                2490                2510
TTTCAGCCTGTTTTTAAGATAAATTCAAAAGGTGAAAATATCTTAGGTCACACAGCACCA
 F  Q  P  V  F  K  I  N  S  K  G  E  N  I  L  G  H  T  A  P
         2530                2550                2570
TTCCCTGAAGACATTCCAAGATTTGTTGCTAATGTGTTTACAAAACATGATAATGATATA
 F  P  E  D  I  P  R  F  V  A  N  V  F  T  K  H  D  N  D  I
         2590                2610                2630
ATATTAGATCCATTTTCAGGCTCATTAACTTCAGCTATAGCTTCGTATAAAAGCAATAGA
 I  L  D  P  F  S  G  S  L  T  S  A  I  A  S  Y  K  S  N  R
         2650                2670                2690
ATAGGTCTTGGAATTGAGTTGTCTCCTGATTATGTTGAATTATCTAGGGACAGAGCGTTA
 I  G  L  G  I  E  L  S  P  D  Y  V  E  L  S  R  D  R  A  L
         2710                2730
TTAGAAGGGGTAACTACTAAAATTTTAAATTTTAATTAA
 L  E  G  V  T  T  K  I  L  N  F  N  *
```

FIG. 2

```
              10                  30                  50
ATGGAACGTCAATTAAAATCAATTGCTTACGCTTTTGTTGCAAACGATATAGATGTGTAT
 M  E  R  Q  L  K  S  I  A  Y  A  F  V  A  N  D  I  D  V  Y
              70                  90                 110
ATACCAGATGGAGAATCAAATTGTATAGTGGTAACCAAATTGGTTTGCAAGGATTGCGGG
 I  P  D  G  E  S  N  C  I  V  V  T  K  L  V  C  K  D  C  G
             130                 150                 170
CAATATTGGCATACTAGCTTATCAGAGTGTTATTTTTGTGGTACTTTGAATTTTTATCTA
 Q  Y  W  H  T  S  L  S  E  C  Y  F  C  G  T  L  N  F  Y  L
             190                 210                 230
TATGAATGTAATTCTTGTGGAAAAAAATATTCATTAACTTcTTCTTCAAAATCTTGTGAT
 Y  E  C  N  S  C  G  K  K  Y  S  L  T  S  S  S  K  S  C  D
             250                 270                 290
ACTGATGGTTGTAATGGTAAATTAATCAAAAGATGTAGCAATCCAGAATGTATTAGTCGG
 T  D  G  C  N  G  K  L  I  K  R  C  S  N  P  E  C  I  S  R
             310                 330                 350
ACAAATGAAGAAATACAGCGTGCAACAGATGAGCAAGGAGGAGTATTTGATCTCAATTCA
 T  N  E  E  I  Q  R  A  T  D  E  Q  G  G  V  F  D  L  N  S
             370                 390                 410
TCTTTTAACGTATCTTTAAATCATTGTGTGACATGTGGAAGTAAAGAAAACTATTACAAA
 S  F  N  V  S  L  N  H  C  V  T  C  G  S  K  E  N  Y  Y  K
             430                 450                 470
ACATATCGTATATACTCTTATCGAACGGAAGTAGAACCAAATATAGAAGCTTTAAGAGAG
 T  Y  R  I  Y  S  Y  R  T  E  V  E  P  N  I  E  A  L  R  E
             490                 510                 530
TTTGCCAATAACAACAAACTTAATAGTGATGAAGATGTTATAATCATTAAACACCTAGTT
 F  A  N  N  N  K  L  N  S  D  E  D  V  I  I  K  H  L  V
             550                 570                 590
GATAATGTAATTCATTACGGTTATATTCCATACAGTAAGTTAGATGAAACAACAGAAATT
 D  N  V  I  H  Y  G  Y  I  P  Y  S  K  L  D  E  T  T  E  I
             610                 630                 650
ACTACAACATTTTCTCGTTTTTCTGATCTTGTTTCAGAATTGTTCCCAGTTAACGTTCCT
 T  T  T  F  S  R  F  S  D  L  V  S  E  L  F  P  V  N  V  P
             670
CCAAATGTTACTGAATAA
 P  N  V  T  E  *
```

FIG. 3

```
          10                  30                  50
ATGGAACAACAAAAATTCCCTAATCCAAGAATTTTTGAGGATATTGATGCAACTGATTTT
 M  E  Q  Q  K  F  P  N  P  R  I  F  E  D  I  D  A  T  D  F
          70                  90                 110
TCAAAACATAATAAAAAGCATGTAACAGAGGACTTTGTGGCTGAAAACTTTAAAGATGTT
 S  K  H  N  K  K  H  V  T  E  D  F  V  A  E  N  F  K  D  V
         130                 150                 170
GGTTGGAGAGTTTATCGTCCTTTTAACGATACAGGAATTGATCTTATTGCCAAGAAATTT
 G  W  R  V  Y  R  P  F  N  D  T  G  I  D  L  I  A  K  K  F
         190                 210                 230
GTATGTCCTGATGGACATACAAAGTGGAATCAAAATCTAACAAAAGAAATGACTTGTAGT
 V  C  P  D  G  H  T  K  W  N  Q  N  L  T  K  E  M  T  C  S
         250                 270                 290
GAATGCGGAAAATCATTAATTGAAATAACACGTTTTATTCAAGTAAAAACTCGGGAAGTT
 E  C  G  K  S  L  I  E  I  T  R  F  I  Q  V  K  T  R  E  V
         310                 330                 350
AAACAAGTAAAAACTCGGGAAGCTAAAGGAGAAAAGTTTTTTTTCGGTTACACCTTAAAA
 K  Q  V  K  T  R  E  A  K  G  E  K  F  F  F  G  Y  T  L  K
         370                 390                 410
TCAAAGGATTTCCGAACCGATCCTAGACATGTATTTCTCTTATACTCAGATTTTACTATG
 S  K  D  F  R  T  D  P  R  H  V  F  L  L  Y  S  D  F  T  M
         430                 450                 470
GATTTCATTATTCTTCCTATGTATGATTATCTAAACTTGTTTTATACTAACCAAAGTTTA
 D  F  I  I  L  P  M  Y  D  Y  L  N  L  F  Y  T  N  Q  S  L
         490                 510                 530
GGCTCAACACACTTTAGTACCCCTTCTTTTCGCCAAGGGAATAATAAACTGAACGGTCTT
 G  S  T  H  F  S  T  P  S  F  R  Q  G  N  N  K  L  N  G  L
         550                 570                 590
TCGAAAGACAAGAATGATAACTGGGTTTGGAGTGGAGTTTCGTTTAATGAATTCGTAAAT
 S  K  D  K  N  D  N  W  V  W  S  G  V  S  F  N  E  F  V  N
         610                 630                 650
GAAAAAGGTATGGATAAACTTAGCTGTCCAATCTACGATATTGAATTAGAGAGCTATACT
 E  K  G  M  D  K  L  S  C  P  I  Y  D  I  E  L  E  S  Y  T
         670                 690                 710
AAGAAAATACAAGAATTAAAATTTAGCTTATTCTATCGGTACTCTCCTGGTAGAAAAAAT
 K  K  I  Q  E  L  K  F  S  L  F  Y  R  Y  S  P  G  R  K  N
         730                 750                 770
CAGGTATCAGCTCCTACTGTCGAATTTATTAATAATCATTTAGCATTTTTATAAGTCTA
 Q  V  S  A  P  T  V  E  F  I  N  N  H  F  S  I  F  I  S  L
         790                 810                 830
CCAAAGGAAGCTATTGCTAGCAAAAGGAAGGCACATCTTGAAAGCCTACGTCAAGATCTC
 P  K  E  A  I  A  S  K  R  K  A  H  L  E  S  L  R  Q  D  L
         850                 870                 890
CCAGAAGATTTGAAAAAGAGTGTTAACGAAGGATACCTAGTCAAATTTAAAGGGGTTGAC
 P  E  D  L  K  K  S  V  N  E  G  Y  L  V  K  F  K  G  V  D

TTATAA
 L  *
```

METHOD FOR CLONING AND PRODUCING THE BSlI RESTRICTION ENDONUCLEASE IN *E. COLI*

BACKGROUND OF THE INVENTION

The present invention relates to recombinant DNA which encodes the BslI restriction endonuclease as well as BslI methylase, and the production of BslI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, *Nucl. Acids Res.* 24:223–235, (1996)).

Restriction endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTTAAA3', 5'PuGGNCCPy3' and 5'CACNNNGTG3' respectively. *Escherichia coli* RY13, on the other hand, produces only one enzyme, EcoRI, which recognizes the sequence 5'GAATTC3'.

A second component of bacterial restriction-modification (R-M) systems are the methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is now possible to clone genes and overproduce the enzymes in large quantities. The key to isolating clones of restriction endonuclease genes is to develop a simple and reliable method to identify such clones within complex 'libraries', i.e. populations of clones derived by 'shotgun' procedures, when they occur at frequencies as low as.$10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Mol. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985)).

A third approach, and one that is being used to clone a growing number of R-M systems are now being cloned by selection for an active methylase gene (U.S. Pat. No. 5,200,333 and BsuRI: Kiss et al., *Nucl. Acids. Res.* 13:6403-6421, (1985)). Since R-M genes are often closely linked, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983); and MspI: Walder et al., *J. Biol. Chem.* 258:1235–1241, (1983)).

A more recent method, the "endo-blue method", has been described for direct cloning of restriction endonuclease genes in *E. coil* based on the indicator strain of *E. coli* containing the dinD::lacZ fusion (Fomenkov et al., U.S. Pat. No. 5,498,535; Fomenkov et al., *Nucl. Acids Res.* 22:2399–2403, (1994)). This method utilizes the *E. coli* SOS response following DNA damages caused by restriction endonucleases or non-specific nucleases. A number of thermostable nuclease genes (Tth111I, BsoBI, Tf nuclease) have been cloned by this method (U.S. Pat. No. 5,498,535).

Because purified restriction endonucleases, and to a lesser extent, modification methylases, are useful tools for creating recombinant molecules in the laboratory, there is a commercial incentive to obtain bacterial strains through recombinant DNA techniques that produce these enzymes in large quantities. Such overexpression strains would also simplify the task of enzyme purification.

SUMMARY OF THE INVENTION

The methylase selection method was used to clone the BslI methylase gene (bslIM) from *Bacillus species*. Using methylase selection, however, only a partially active BslI methylase lacking the 17 amino acid residues at the N-terminus was obtained and cloned in *E. coli* using expression vector pRRS. Once it was determined that only a partially active methylase clone had been obtained, inverse PCR was used to clone the missing portion of the BslI methylase.

After cloning the complete BslI methylase gene and its upstream DNA sequences, a RadC homolog was found upstream of the BslI methylase. Because methylase and restriction endonuclease genes are usually located in proximity to each other in a particular restriction-modification system, efforts were made to clone the downstream DNA by inverse PCR. After two round of inverse PCR reactions, two open reading frames (ORF) were found downstream of the BslI methylase gene. Expression of the first ORF (ORF1) in a T7 expression vector did not yield any active BslI endonuclease. Expression of the second ORF (ORF2) in E. coli and assay of the crude cell extract indicated that this gene product has DNA nicking activity. However, the gene product of ORF2 alone does not constitute BslI endonuclease activity.

Native BslI restriction endonuclease was purified to near homogeneity from Bacillus sp. cell extract. Two major protein bands (approximately 25 kDa and 35 kDa) were found in an SDS-PAGE gel. Amino acid sequence of the two proteins was determined and the N-terminal amino acid sequences were found to closely match the amino acid sequence predicted from the DNA encoding ORF1 and ORF2. This was the first time one restriction enzyme has been found which consists of two different subunits. BslI restriction endonuclease genes ORF1 and ORF2 overlap by 1 base and run in the opposite direction of the BslI methylase gene. When both genes (ORF1 and ORF2) are cloned into a T7 expression vector and transformed into BslI methylase premodified cells, $2–10^5$ to $2 \times 10^6$ units of BslI endonuclease are produced per gram of wet E.coli cells following IPTG induction. The recombinant BslI endonuclease is purified by chromatography to near homogeneity. When analyzed in an SDS-PAGE gel, the recombinant BslI endonuclease also consists of two subunits, 25.6 kDa and 35.3 kDa respectively.

BRIEF DESCRIPTION OF THE DRAWINGS

FIG. 1. BslI methylase gene (SEQ ID NO:1) and its encoded amino acid sequence (SEQ ID NO:2).

FIG. 2. ORF1 of BslI endonuclease gene (SEQ ID NO:3) and its encoded amino acid sequence (SEQ ID NO:4).

FIG. 3. ORF2 of BslI endonuclease gene (SEQ ID NO:5) and its encoded amino acid sequence (SEQ ID NO:6).

DETAILED DESCRIPTION OF THE INVENTION

Figure 4:
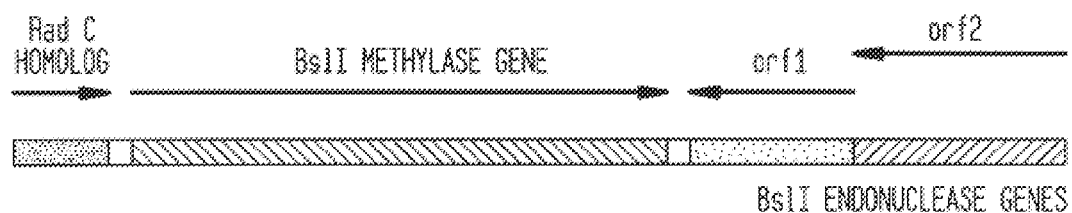
FIG. 4. Gene organization of BslI restriction-modification system.
Figure 5:
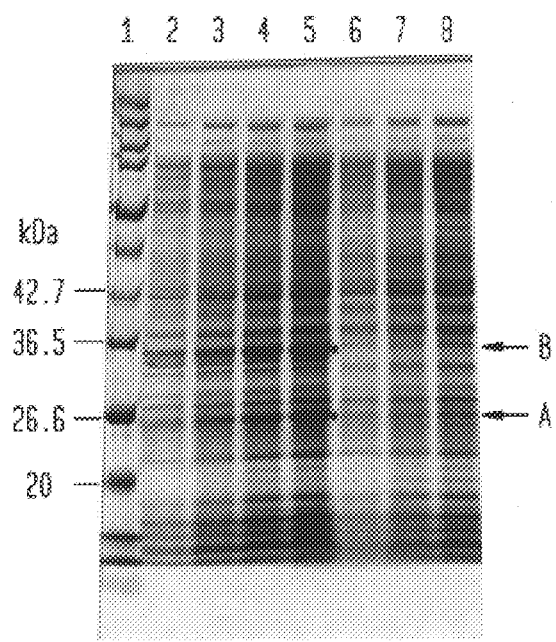
FIG. 5. SDS-PAGE gel of IPTG-induced cell extracts containing BslI restriction endonuclease. Lane 1, Protein size marker; Lanes 2, 3, 4, and 5, IPTG induced cell extract; Arrows A and B indicated the induced proteins, 35.3 kDa and 25.6 kDa, respectively. Lanes 6, 7, and 8, non-induced cell extracts.

The method described herein by which the BslI methylase gene and the BslI restriction endonuclease genes are preferably cloned and expressed in E. coli employs the following steps:

1. Construction of a Sau3AI partial genomic DNA library.

Bacillus sp genomic DNA was digested with Sau3AI to achieve the desired partial digestion. The Sau3AI partially digested genomic DNA in the range of 2–5 kb was gel-purified and ligated into BamHI cut and CIP treated vector pRRS at 16° C. overnight. Transformation and electroporation was carried out using RR1 competent cells and ligated DNA. The transformants were pooled and amplified. Plasmid DNA was prepared from the overnight cell cultures.

2. Challenge the Sau3AI partial library DNA with BslI digestion and cloning of BslI methylase gene.

The Sau3AI partial library DNA was digested with BslI at 55° C. overnight. The digested DNA was used to re-transform RR1 competent cells. Plasmid DNA was isolated from cell culture of all transformants. Individual plasmid DNA was digested with BslI to detect any resistance to digestion. One plasmid isolate #27 displayed partial resistance to BslI digestion. The degree of resistance to BslI digestion was very partial, suggesting that either the cloned BslI methylase gene was poorly expressed in E. coli or a truncated BslI methylase gene was cloned that is still partially active (after sequencing the insert it was found that a truncated BslI methylase gene was cloned, see Example 1).

3. Subcloning and sequencing of the insert carrying the BslI methylase gene

Two EcoRI fragments, five HindIII fragments and two NdeI fragments derived from the original insert were gel-purified and subcloned in pUC19. The original isolate #27 plasmid DNA and all the EcoRI, HindIII, and NdeI subclones were sequenced using pUC19 forward and reverse primers. Mung bean nuclease and Exonuclease III treated deletion clones were also constructed by serial deletion of #27 insert and were subjected to DNA sequencing. The entire insert was sequenced and the insert has 3063 bp that encode two partial open reading frames. When the large ORF was compared to the known gene in GenBank using blastx, it shows homology to known N4 cytosine methylases. The truncated BslI methylase gene lacks the ATG (Met) start codon at the N-terminus.

To clone the missing portion of the BslI methylase, Bacillus sp. genomic DNA was amplified by inverse PCR. Inverse PCR products were found in self-ligated DNA of HinfI, HpaII, MfeI, NdeI, RsaI, SspI, TfiI cleaved DNA. Inverse PCR products were gel-purified from PCR reactions of HpaII, MfeI, and SspI cleaved and self-ligated DNA. The inverse PCR products were sequenced. Five hundred and sixty five (565) bp of new sequence was derived from DNA sequencing of HpaII and SspI inverse PCR products. An ATG start codon was found in the newly derived sequence. Seventeen codons were found upstream of the original isolate of the truncated methylase gene. The rest of the new DNA upstream of the BslI methylase gene encodes a RadC homolog. Since restriction-modification genes are usually located in proximity to each other, it was reasoned that the BslI endonuclease gene should be located downstream of the methylase gene.

4. Cloning of BslI restriction endonuclease gene

Inverse PCR was carried out to clone the genomic DNA downstream of the BslI methylase gene. Inverse PCR products were obtained from RsaI cut and self-ligated template DNA. The DNA fragment was gel-purified and sequenced. The newly derived DNA sequence extended out further by 188 base pairs.

To clone the DNA further downstream, a second set of primers were made based on the newly cloned 188 bp sequence. Inverse PCR products were found in AflIII, NlaIII, HindIII, and TaqI cleaved and self-ligated DNA. The inverse PCR products were gel-purified and sequenced. The newly-derived sequence further extended out 1270 bp. Translation of this DNA sequence in six reading frames indicated that there are two open reading frames downstream of the BslI methylase genes. The two ORFs overlap by 1 base (see FIG. 4 for gene organization). These two genes are transcribed in the direction opposed to the BslI methylase gene.

5. Expression of BslI methylase gene in E. coli

The entire BslI methylase gene (2739 bp) was amplified from genomic DNA using Vent® polymerase and two primers in PCR. The PCR product (BslI methylase gene) was digested with BamHI, gel-purified and cloned into pBR322 and T7 expression vector pET21t. Four plasmid isolates displayed full resistance to BslI digestion, indicating modification of BslI sites in vivo via the insertion and expression of the BslI methylase gene.

The BslI methylase (912 aa, molecular mass=105 kDa) is one of the largest methylase gene discovered so far. All the conserved N4 cytosine methylase motifs are located in the C-terminus of the protein. It was thought that the 912-aa methylse may be a fusion of endonuclease and methylase. That is, the N-terminal half may encode the endonuclease function and the C-terminal half may encode the methylase function. To test this possibility, the 2739 bp PCR DNA was cloned into the T7 expression vector pET21t. Cells containg pET21t plus 2739 bp insert were induced with IPTG. Cells extracts were assayed for BslI endonuclease activity. No BslI endonuclease activity was ever detected. It was concluded that the 2739 bp DNA only encodes BslI methylase activity.

To test the function of the N-terminal part of the BslI methylase in vivo, a 1257 bp deletion (419 aa deletion) was constructed by deleting the ClaI and BsrGI fragment of pBR322-BslIM. This deletion abolished the BslI methylase activity in vivo.

The BamHI fragment containing BslI methylase gene was also inserted into pACYC184. The resulting plasmid pACYC-BslIM was also resistant to BslI digestion.

6. Expression of ORF1 (25.6 kDa) in T7 expression vector pACYC-T7

PCR was carried out to amplify ORF1 gene. The PCR product was digested with BamHI and gel-purified. The ORF1 DNA fragment was cloned into BamHI cut and CIP treated pACYC-T7. Ten plasmids with insert were isolated. Cell extracts were prepared from IPTG-induced cells ER2566 [pBR-BslIM, pACYC-T7-ORF1]. Cell extracts were used to assay for BslI endonuclease activity. The assay failed to detect any DNA cleavage activity in the cell extract. Initially, it was concluded that ORF1 (25.6 kDa) did not confer BslI endonuclease activity, which was surprising in view of its proximity to the methylase gene. The ORF1 region was thereafter analyzed to determine if it acted as a control or "C" gene which occur in some systems. It did not correspond to known "C" genes. Later, as discussed below, it was determined that both ORF1 and ORF2 gene products comprise the active endonuclease.

7. Expression of ORF2 (35.3 kDa) in T7 expression vector pAII17

PCR was performed to amplify ORF2 gene. The PCR DNA was digested with NdeI and BamHI at 37° C. for 3.5 h and the resulting DNA was cloned into NdeI and BamHI cut pAII17 expression vector. ER2566 [pACYC-BslIM, pAII17-ORF2] cells were induced with IPTG. Cell lysates were prepared and assayed for BslI endonuclease activity on pUC19 substrate DNA (there are six BslI sites in pUC19). Some of the supercoiled pUC19 DNA was converted to linear DNA. Similarly, it was concluded that the 35.3 kDa protein, while possessing DNA nicking activity (non-specific nuclease activity), did not possess BslI restriction endonuclease activity.

8. N-terminal amino acid sequencing of the native BslI restriction endonuclease

The native BslI endonuclease was purified to near homogeneity and the purified protein was subjected to SDS-PAGE initially, in order to provide useful information for expression. Fortuitously, the information obtained from the sequence helped unravel these perplexing findings. Surprisingly, two major protein bands were detected with molecular mass of approximately 25 kDa and 35 kDa. The N-terminal amino acid sequence of the protein was determined as (M)EQQXXPNPXIFXXID 35 kDa (X=unclear amino acid residues) (SEQ ID NO:7). The N-terminal amino acid sequence of the protein was determined as (M)EXQLXSIXXXFVANDID 25 kDa (X=unclear amindo acid residues) (SEQ ID NO:8). The N-terminal aa sequence of the 35 kDa protein predicted from the coding DNA sequence is as follows: MEQQKFPNPRIFEDID (SEQ ID NO:9). This sequence matches closely with the actual N-terminal amino acid sequence of the native protein (M)EQQXXPNPX IFXXID (SEQ ID NO:7)]. The N-terminal aa sequence of the 25 kDa protein predicted from the DNA sequence is: MERQLKSIAYAFVANDID (SEQ ID NO:10), which matches well with the actual aa sequence of the native protein (M)EXQLXSIXXXFVANDID (SEQ ID NO:8)]. It was concluded that BslI restriction endonuclease consists of two different subunits, 35 kDa and 25 kDa respectively. This is the first time a restriction endonuclease has been found to possess two unique subunits.

9. Expression of ORF2 and ORF1 together in T7 expression vector pAII17

Two primers were synthesized for PCR amplification of both ORF2 and ORF1. PCR was carried out and the PCR product was digested with NdeI and BamHI and then ligated into NdeI and BamHI cut pAII17 vector. ER2566 [pACYC-BslIM, pAII17-BslIR (QRF2 & ORF1)] cells were induced by addition of IPTG. Cell extract were assayed on λ DNA and pUC19 DNA substrates for BslI endonucleas activity at 55° C. for 1.5 h. All five cell extracts (#2, #8, #9, #16. #17) displayed BslI endonuclease activity. Isolate #8 and #9 displayed high activity in cell extract prepared from 500 ml of IPTG-induced cells. The enzyme activity yield is about $2 \times 10^6$ units/gram of wet E. coli cells (IPTG-induced). When cell cultures were made from 1 week old plate or 1 week old liquid culture, the BslI activity dropped 10-fold to about $2 \times 10^5$ units BslI/gram of wet E. coli cells. Introduction of a third plasmid pLysS did not further stabilize the overexpression construct (ER2504 [pLysS, pLG339-BslM, pAII17-BslIR (ORF2 & ORF1)]). When the PCR DNA fragment containing ORF2 and ORF1 was inserted in a $P_{tac}$ expression vector pAGR3 (Jack et al, Nucl. Acids Res., 19:1825–1829 (1991)), the BslI yield was 100-fold lower compared to the T7 expression construct.

10. Purification of BslI restriction endonuclease

The recombinant BslI endonuclease was purified by chromatography through Heparin Sepharose® and Q Sepharose® columns.

The present invention is further illustrated by the following Examples. These Examples are provided to aid in the understanding of the invention and are not construed as a limitation thereof.

The references cited above and below are herein incorporated by reference.

EXAMPLE 1

CLONING OF BSLI RESTRICTION-MODIFICATION SYSTEM IN E.coli

Genomic DNA was prepared from Bacillus species (this strain is in the New England Biolabs' collection, NEB #606, Beverly, Mass.; Cowan et al, unpublished result).

1. Construction of a Sau3AI partial genomic DNA library

Five μg of Bacillus sp genomic DNA was digested with 2, 1, 0.5, 0.25 and 0.125 units of Sau3AI at 37° C. for 30 min.

0.5 and 0.25 units of digestion gave rise to the desired partial digestion. The Sau3AI partially digested genomic DNA in the range of 2–5 kb was gel-purified in a 1% low melting agarose gel. The purified genomic DNA was ligated into BamHI cut and CIP treated vector pRRS (Skoglund et al, Gene, 88:1–5 (1990)) at 16° C. overnight. Transformation was carried out by mixing RR1 (TonA−, DnaseI−) competent cells and the ligated DNA by the standard procedure. Transformants were plated on LB agar plus Amp (100 μg/ml). About 5000 colonies were obtained in transformation. To increase the number of colonies, electroporation was carried out using electro-competent RR1 (TonA−, DnaseI−) cells and ligated DNA. About 50,000 transformants were obtained. All the transformants were pooled and inoculated into 1 liter of LB broth plus Amp and incubated at 37° C. overnight. Plasmid DNA was prepared from the overnight cells by Qiagen (Chatsworth,Calif.) midi columns.

2. Challenge the Sau3AI partial library DNA with BslI digestion and cloning of BslI methylase gene 0.2, 0.5 and 1 μg of the Sau3AI partial library DNA was digested with 25 units of BslI at 55° C. overnight. The digested DNA was used to re-transform RR1 (TonA−, DnaseI−) competent cells. One hundred and twenty six transformants were obtained. Mini-preparation of plasmid DNA was isolated from 2 ml cell culture of all 126 transformants. Individual plasmid DNA was digested with BslI to detect any resistance to digestion. One plasmid isolate #27 displayed partial resistance to BslI digestion. The degree of resistance to BslI digestion was very partial, suggesting that either the cloned BslI methylase gene was poorly expressed in E. coli or a truncated BslI methylase gene was cloned due to Sau3AI partial digestion that is still partially active (after sequencing the insert it was found that a truncated BslI methylase gene was cloned. See Section 3). To determine if #27 isolate was truly resistant to BslI digestion, the plasmid was digested with 1, 2.5, 5, 7.5 and 10 units of BslI at 55° C. for 2 hours. It was found that #27 plasmid showed same level of partial resistance with 1 to 10 units of BslI digestion. The partial resistance was truly conferred by the presence of the partially active BslI methylase and was not due to contaminants that inhibit BslI digestion.

Restriction digestion of #27 plasmid DNA with AatII, AflIII, AlwNI, EcoRI, Eco0109I, HincII, HindIII, NarI, NdeI PstI, SapI, SalI, SmaI, SphI, SspI and XbaI indicated that it contains an insert of approximately 3 kb DNA.

3. Subcloning and sequencing of the insert carrying the BslI methylase gene

27 plasmid DNA was digested with EcoRI, HindIII and NdeI respectively. Two EcoRI fragments, five HindIII fragments and two NdeI fragments derived from the insert were gel-purified and subcloned in pUC19. The original isolate #27 plasmid DNA and all the EcoRI, HindIII, and NdeI subclones were sequenced using pUC19 forward and reverse primers. Mung bean nuclease and Exonuclease III treated deletion clones were also constructed by serial deletion of #27 insert and were subjected to DNA sequencing. Six primers were synthesized to sequence the non-overlapping region or to confirm the complementary strand of the known sequence. The entire insert was sequenced and the insert has 3063 bp that encode two partial open reading frames. When the large ORF was compared to the known gene in GenBank using blastx, it shows homology to known N4 cytosine methylases. All the N4 cytosine methylase conserved motifs are located in the C-terminus. The N-terminus region does not show any homology to known proteins. The truncated BslI methylase gene lacks the ATG (Met) start codon at the N-terminus. Presumably it's translation initiated from the upstream lacZα gene in the multiple cloning sites of vector pRRS.

To clone the missing portion of the BslI methylase, Bacillus sp. genomic DNA was amplified by inverse PCR. Bacillus sp genomic DNA was cleaved with ApoI, AseI, BsrGI, EarI, EcoRV, HaeII, HhaI, HincII, HinfI, HpaII, MfeI, NdeI, PacI, RsaI, ScaI, SspI, TfiI, and XhoI, respectively. The restriction enzyme cleaved DNA was self-ligated at a low concentration (2 μg/ml) and the self-ligated circular molecules were used as templates in inverse PCR using a set of primers:
5' AGCATCCTCATCAATCAAAGATACTAC 3' (166-62) (SEQ ID NO:11)
5' GCTTGAAGAACAATTCCCTAAGGCATT 3' (166-63) (SEQ ID NO:12)

Inverse PCR conditions 95° C. 1' 55° C. 1', 72° C. 2', 30 cycles were employed. Inverse PCR products were found in self-ligated DNA of HinfI, HpaII, MfeI, NdeI, RsaI, SspI, TfiI cleaved DNA. Inverse PCR products were gel-purified from PCR reactions of HpaII, MfeI, and SspI cleaved and self-ligated DNA. DNA sequencing was performed using primer 166-62 or 166-63. Five hundred and sixty five (565) bp of new sequence was derived from DNA sequencing of HpaII and SspI inverse PCR products. An ATG start codon was found in the newly derived sequence. Seventeen codons were found upstream of the original truncated methylase gene. The rest of the new DNA upstream of the BslI methylase gene encodes a RadC homolog. Since restriction-modification genes are located in proximity to each other, it was reasoned that the BslI endonuclease gene should be located downstream of the methylase gene.

4. Cloning of BslI restriction endonuclease gene

Inverse PCR was carried out to clone the genomic DNA downstream of the BslI methylase gene. A set of inverse PCR primers were made based on the end of BslI methylase gene:
5' CTGGGAACAATTCTGAAACAAGATCAG 3' (163-192) (SEQ ID NO:13)
5' ACAGGATCCCTAATTAAAATTTAAAATTTTAGTAGTTAC 3' (166-114, italicized bases are non-coding sequence) (SEQ ID NO:14)

Bacillus sp. genomic DNA was digested with RsaI, EaeI, HaeII, HaeIII, HhaI, HinfI, HinPlI, HpaII, MspI, NdeI, and SspI respectively. The restriction enzyme digested DNA was self-ligated and the ligated circular molecules were used as templates for inverse PCR. Inverse PCR was preformed at 95° C. 1', 55° C. 1', 72° C. 2' for 30 cycles using primers 163-192 and 166-144. Inverse PCR products were obtained from RsaI cut and self-ligated template DNA. The DNA fragment was gel-purified and sequenced using primers 163-192. The newly derived DNA sequence extended out further 188 bp.

To clone the DNA further downstream, a second set of primers were made based on the newly cloned 188 bp sequence as follows:
5' CATATAGATAAAAATTCAAAGTAC 3' (168-79) (SEQ ID NO:15)
5' AATGTAATTCTTGTGGAAAAAAATATT 3' (168-80). (SEQ ID NO:16)

Bacillus sp genomic DNA was digested with AflIII, AseI, BfaI, BstYI, Cac8I, HincII, HindIII, HpaI, MseI, NlaIII, PacI, Sau3AI, SspI, TaqI and XmnI respectively. The resulting DNA was self-ligated. Primers 168-79 or 169-80 were used to amplify the adjacent DNA under inverse PCR conditions of 95° C. 1', 50° C. 1', 72° C. 3' for 35 cycles. Inverse PCR products were found in AflIII, NlaIII, HindIII, and TaqI cleaved and self-ligated DNA. The inverse PCR products were gel-purified and sequenced using primer 168-79 and 168-80. The newly-derived sequence further extended out 1270 bp. Translation of this DNA sequence in six reading frames indicated that there are two open reading frames downstream of the BslI methylase genes. The two ORFs overlap by 1 base (see FIG. 4 for gene organization). These two genes are transcribed in the direction as opposed to the BslI methylase gene.

5. Expression of BslI methylase gene in *E. coli*

The entire BslI methylase gene (2739 bp) was amplified from genomic DNA using Vent® polymerase and two primers in PCR (95° C. 1', 55° C. 1', 72° C. 3', 20 cycles). The two primer sequences are:

5' AATGGATCCGGAGGTATAATAATGAAT-TGGATATTTAATACTCTGATT 3' (166-144) (SEQ ID NO:17)

5' ACAGGATCCCTAATTAAAATT-TAAAATTTTAGTAGTTAC 3' (166-114). (SEQ ID NO:18)

The PCR product (BslI methylse gene) was digested with BamHI, gel-purified and cloned into pBR322 and T7 expression vector pET21t. Fourteen plasmids containing the methylase gene insert were digested with BslI. Four isolates displayed full resistance to BslI digestion, indicating modification of BslI sites in vivo via the insertion and expression of the BslI methylase gene.

The BslI methylase (912 aa, molecular mass=105 kDa) is one of the largest methylase gene discovered so far. All the conserved N4 cytosine methylase motifs are located in the C-terminus of the protein. It was thought that the 912-aa methylse may be a fusion of endonuclease and methylase. That is, the N-terminal half may encode the endonuclease function and the C-terminal half may encode the methylase function. To test this possibility, the 2739 bp PCR DNA was cloned into the T7 expression vector pET21t. Cells containg pET21t plus 2739 bp insert were induced with IPTG. Cells extracts were assayed for BslI endonuclease activity. No BslI endonuclease activity was ever detected. It was concluded that the 2739 bp DNA only encodes BslI methylase activity.

To test the function of the N-terminal part of the BslI methylase in vivo, a 1257 bp deletion (419 aa deletion) was constructed by deleting the ClaI and BsrGI fragment of pBR322-BslIM. This deletion abolished the BslI methylase activity in vivo. The plasmid with the desired deletion did not modify BslI sites in vivo and therefore it was sensitive to BslI digestion.

The BamHI fragment containing BslI methylase gene was also inserted into pACYC184. The resulting plasmid pACYC-BslIM was also resistant to BslI digestion.

6. Expression of ORF1 (25.6 kDa) in T7 expression vector pACYC-T7

To express the putative endonuclease ORF1 (25.6 kDa), a low copy number T7 expression vector was constructed. The EagI-HindIII fragment of pACYC184 was replaced by the EagI-HindIII fragment from pET11d that carries the T7 promoter and transcription terminator. The single BamHI site downstream of T7 promoter was used for cloning insert DNA. Two PCR primers were synthesized as follows:

5' AGAGGATCCGGAGGTAATAAAATG-GAACGTCAATTAAAATCAATTGCTTAC.3' (169-71) (SEQ ID NO:19)

5' CTAGGATCCTTATTCAGTAACATTTG-GAGGAACGTT 3' (168-76). (SEQ ID NO:20)

PCR was carried out using Vent® polymerase, primers 167-71 and 168-76 under conditions of 95° C. 1', 60° C. 1', 72° C. 1', 20 cycles. The PCR product was digested with BamHI and gel-purified. The ORF1 DNA fragment was cloned into BamHI cut and CIP treated pACYC-T7. Ten plasmids with insert were isolated. Cell extracts were prepared from IPTG-induced cells ER2566 [pBR-BslIM, pACYC-T7-ORF1]. Four µl of the cell extract were used to digest 1 µg of λ DNA at 55° C. for 1 h. The assay failed to detect any DNA cleavage activity in the cell extract. It was concluded that ORF1 (25.6 kDa) alone does not confer BslI endonuclease activity.

7. Expression of ORF2 (35.3 kDa) in T7 expression vector pAII17

Expression vector pAII17 is a modified pET11 T7 expression vector that contains four copies of transcription terminators upstream of T7 promoter (Kong et al. *J. Biol. Chem.* 268:1965–1975 (1993)). Two primers were synthesized for PCR amplification of ORF2 (35.3 kDa):

5' GGAGAGTTACATATGGAACAACAAAAAT-TCCCTAATCCA 3' (172-84) (SEQ ID NO:21)

5' CAAGGATCCAAGCAATTGATTTTAAT-TGACGTTCCA 3' (172-85). (SEQ ID NO:22)

PCR was performed using Vent® polymerase, primers 172-84 and 172-85 (95° C. 1', 60° C. 1', 72° C. 1', 20 cycles). The PCR DNA was digested with NdeI and BamHI at 37° C. for 3.5 h and the resulting DNA was cloned into NdeI and BamHI cut pAII17 expression vector. ER2566 [pACYC-BslIM, pAII17-ORF2] cells were induced with IPTG. Cell lysates were prepared and assayed for BslI endonuclease activity on pUC19 substrate DNA (there are six BslI sites in pUC19). Some of the supercoiled pUC19 DNA was converted to linear DNA. It was concluded that the 35.3 kDa protein possesses the DNA nicking activity, but it alone does not constitute BslI restriction endonuclease activity.

8. N-terminal amino acid sequencing of the native BslI restriction endonuclease

The native BslI endonuclease was purified to near homogeneity and the purified protein was subjected to SDS-PAGE. Two major protein bands were detected with molecular mass of approximately 25 kDa and 35 kDa. The N-terminal amino acid sequence of the 35 kDa protein was determined as (M)EQQXXPNPXIFXXID (X=unclear amino acid residues (SEQ ID NO:7)). The N-terminal amino acid sequence of the 25 kDa protein was determined as (M)EXQLXSIXXXFVANDID (X=unclear amindo acid residues) (SEQ ID NO:8). The N-terminal aa sequence of the 35 kDa protein predicted from the coding sequence is as follows: MEQQKFPNPRIFEDID (SEQ ID NO:9). This sequence matches closely with the actual aa sequence of the native protein (M)EQQXXPNPXIFXXID (SEQ ID NO:7)]. The N-terminal aa sequence of the 25 kDa protein translated from the DNA sequence is: MERQLKSIAYAFVANDID (SEQ ID NO:10), which matches well with the actual aa sequence of the native protein (M)EXQL XSIXXXFVAN-DID (SEQ ID NO:8)]. It was concluded that BslI restriction endonuclease is consisted of two different subunits, 35 kDa and 25 kDa respectively. This is the first discovery that restriction endonuclease is comprised of two unique subunits.

9. Expression of ORF2 and ORF1 together in T7 expression vector pAII17

Two primers were synthesized for PCR amplification of both ORF2 and ORF1.

5' GGAGAGTTACATATGGAACAACAAAAAT-TCCCTAATCCA 3' (172-84) (172-84 is the same primer as 172-84 in Section 7) (SEQ ID NO:23).

5' CTAGGATCCTTATTCAGTAACATTTG-GAGGAACGTT 3' (168-76) (168-76 is the same primer as 168-76 in Section 6) (SEQ ID NO:24)

PCR was carried out using Vent® polymerase, primers 172-84 and 168-76 (95° C. 1', 60° C. 1', 72° C. 2', 20 cycles). The PCR DNA was digested with NdeI and BamHI at 37° C. for 3.5 h. The DNA was purified by phenol-CHCl$_4$ extraction, ethanol precipitation, and then ligated into NdeI and BamHI cut pAII17 vector. A total of five isolates (#2, #8, #9, #16, #17) with insert were found in plasmid DNA mini-preparation. ER2566 [pACYC-BslIM, pAII17-BslIR (ORF2 & ORF1)] cells were grown in 10 ml LB+Amp+Cm to late log phase and induced by addition of IPTG (final 0.5 mM concentration) for 2 h. The induced cells were harvested and resuspended in 1 ml sonication buffer (50 mM Tris-HCl, pH 8, 10 mM β-mercaptoethanol). Cells were lysed by sonication. Following centrifugation to remove all debris cell extract was assayed on λ DNA and pUC19 DNA substrates for BslI endonuclease activity at 55° C. for 1.5 h. All five cell extract (#2, #8, #9, #16. #17) displayed BslI endonuclease activity. Isolate #8 and #9 displayed high activity in cell extract prepared from 500 ml of IPGT-induced cells. The enzyme activity yield is about $2\times10^6$ units/gram of wet E. coli cells (IPTG-induced). When cell cultures were made from 1 week old plate or 1 week old liquid culture, the BslI activity dropped 10-fold to about $2\times10^5$ units BslI/gram of wet E. coli cells. Introduction of a third plasmid pLysS did not further stabilize the overexpression construct (ER2504 [pLysS, pLG339-BslM, pAII17-BslIR (ORF2 & ORF1)]). When the PCR DNA fragment containing ORF2 and ORF1 was inserted in a P$_{tac}$ expression vector pAGR3 (Jack et al, Nucl. Acids Res., 19:1825–1829 (1991)), the BslI yield was 100-fold lower compared to the T7 expression construct.

A sample of the E. coli containing ER2566 [pACYC-BslIM, pAII17-BslIR (ORF2 & ORF1)], (NEB#1114) has been deposited under the terms and conditions of the Budapest Treaty with the American Type Culture Collection on Oct. 17, 1997 and received ATCC Accession Number 98559.

10. Purification of BslI restriction endonuclease

Figure 6:
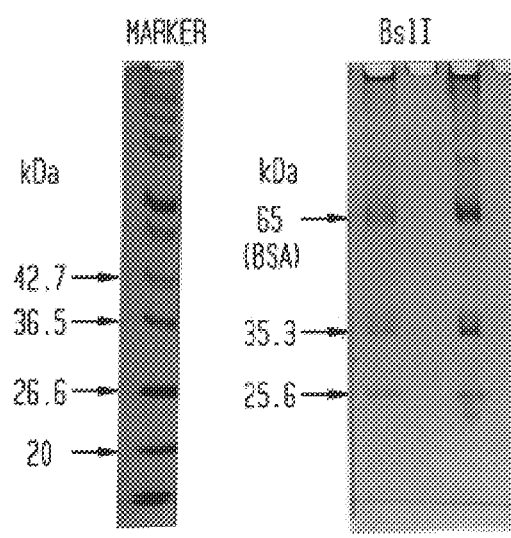
FIG. 6. SDS-PAGE gel of the purified recombinant BslI restriction endonuclease (two subunits: 35.3 and 25.6 kDa, respectively).

The recombinant BslI endonuclease was purified by chromatography through Heparin Sepharose® and Q Sepharose® columns. Forty ml of BslI containing cell extract were loaded onto a Heparin Sepharose® column (2.5×8 cm). The column was washed with buffer A (buffer A: 20 mM Tris-HCl, 0.1M NaCl, 10 mM β-mercaptoethanol, 1 mM EDTA) and proteins were eluted by applying a NaCl gradient of 0.1M to 1.1M. Fractions were assayed for BslI activity on β DNA and those with high activity were pooled and dialysed in buffer A. The BslI protein was further purified through Q Sepharose® column. The final 38 ml of enzyme were concentrated into 10 ml by centrifugation in a centricon. Two $\mu$l, 5 $\mu$l, 10 $\mu$l of the purified enzyme were loaded onto an SDS-polyacrylamide gel and subjected to electrophoresis. The result is shown in FIG. 6. Two major protein bands, 25.6 kDa and 35.3 kDa were detected. The third band is BSA (65 kDa) that was added in the final protein preparation.

11. Re-constitution of BslI restriction endonuclease in vitro.

To re-constitute the BslI restriction endonuclease activity in vitro, the ORF1 gene was amplified in PCR using two primers:

5' GGTTGACTTCATATGGAACGTCAAT-TAAAATCAATTGCT 3' (177-127) (SEQ ID NO:25)

5' CTAGGATCCTTATTCAGTAACATTTG-GAGGAACGTT 3' (168-76). (SEQ ID NO:26)

The ORF1 PCR DNA was cleaved with NdeI and BamHI and cloned into the T7 expression vector pAII17. The resulting strain is ER2566 [pACYC184-BslIM, pAII17-ORF1]. Cell extract was prepared from the IPTG-induced cell culture of ER2566 [pACYC184-BslIM, pAII17-ORF1]. Cell extract was also made from IPTG-induced cells of ER2566 [pACYC184-BslIM, pAII17-ORF2]. Five $\mu$l of each cell extract was mixed and incubated with 1 $\mu$g of pUCl9 DNA at 55° C. for one hour. The DNA substrate was digested into fragments in the same pattern as the positive control of BslI digestion. It was concluded that the BslI restriction endonuclease activity can be re-constituted by mixing gene products of ORF1 and ORF2 in vitro. Gene product of ORF1 or ORF2 alone did not display BslI restriction endonuclease activity.

What is claimed is:

1. Isolated DNA coding for the BslI restriction endonuclease, wherein the isolated DNA is obtainable from *Bacillus Sp.*

2. A recombinant DNA vector comprising a vector into which a DNA segment encoding the BslI restriction endonuclease has been inserted.

3. Isolated DNA encoding the BslI restriction endonuclease and methylase, wherein the isolated DNA is obtainable from ATCC No. 98559.

4. A cloning vector which comprises the isolated DNA of claim 3.

5. A host cell transformed by the vector of claims 2 or 4.

6. A method of producing BslI restriction endonuclease comprising culturing a host cell transformed with the vector of claims 2 or 4 under conditions suitable for expression of said endonuclease.

7. A method of reconstituting a restriction having two different subunits in vitro comprising combining the two subunits that have been expressed separately in *E. coli* host.

* * * * *

UNITED STATES PATENT AND TRADEMARK OFFICE
CERTIFICATE OF CORRECTION

PATENT NO. : 5,866,398

DATED : February 2, 1999

INVENTOR(S) : Xu, et al.

It is certified that error appears in the above-indentified patent and that said Letters Patent is hereby corrected as shown below:

Cover page, Section [54], replace "BS1I" with --BslI--

OTHER PUBLICATIONS, 2nd column, replace "Stankevicius, et al., 1.p.11 "Unique Structure of the TypeII Restriction-Modification System Bpu101" with --Stankevicius, et al., 1.p.11 "Unique Structure of the Type II Restriction-Modification System Bpu10I--.

Column 1, line 1, replace "Bsl1" with --BslI--

Column 8, line 40, replace "ACAGGATCCCT" with
   --*ACAGGATCCCT*--

Column 12, line 6, replace "ß" with --λ--

Column 38, claim 7, line 1, replace "restriction having"
   with --restriction endonuclease having--

UNITED STATES PATENT AND TRADEMARK OFFICE
CERTIFICATE OF CORRECTION

PATENT NO. : 5,866,398

DATED : February 2, 1999

INVENTOR(S) : Xu, et al.

It is certified that error appears in the above-indentified patent and that said Letters Patent is hereby corrected as shown below:

Column 5, line 15, replace "containg" with --containing--

Column 6, line 31, replace "endonucleas" with --endonuclease--

Column 7, line 44, replace "NdeI PstI" with --NdeI, PstI--

Column 9, line 36, replace "containg" with --containing--

Column 11, line 19, replace "IPGT" with --IPTG--

Signed and Sealed this

Sixteenth Day of November, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 2739 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: Coding Sequence
        ( B ) LOCATION: 1...2736
        ( D ) OTHER INFORMATION:

( x i ) SEQUENCE DESCRIPTION: SEQ ID NO:1:

```
ATG  AAT  TGG  ATA  TTT  AAT  ACT  CTG  ATT  CAA  TTT  CTT  GAA  GAT  TTA  AAT         48
Met  Asn  Trp  Ile  Phe  Asn  Thr  Leu  Ile  Gln  Phe  Leu  Glu  Asp  Leu  Asn
1              5                        10                       15
```

| | | | | | | | | | | | | | | | | |
|---|---|---|---|---|---|---|---|---|---|---|---|---|---|---|---|---|
| ATA | GAT | CCG | AGC | GTA | GTA | TCT | TTG | ATT | GAT | GAG | GAT | GCT | AAA | AAG | CTT | 96 |
| Ile | Asp | Pro | Ser<br>20 | Val | Val | Ser | Leu | Ile<br>25 | Asp | Glu | Asp | Ala | Lys<br>30 | Lys | Leu | |
| GAA | GAA | CAA | TTC | CCT | AAG | GCA | TTA | AAA | CAT | CCA | GTT | GTA | GAT | GAG | GAO | 144 |
| Glu | Glu | Gln<br>35 | Phe | Pro | Lys | Ala | Leu<br>40 | Lys | His | Pro | Val | Val<br>45 | Asp | Glu | Glu | |
| ATT | GTA | TAC | AAA | ATA | CTT | TGT | GAA | AAG | TAT | AAT | CTA | AAT | GCT | TTA | AAO | 192 |
| Ile | Val<br>50 | Tyr | Lys | Ile | Leu | Cys<br>55 | Glu | Lys | Tyr | Asn | Leu | Asn<br>60 | Ala | Leu | Asn | |
| GTA | AAA | ACA | ATA | TCT | GAG | ACT | TTA | AAT | AAA | GAA | TAT | AAA | TTT | GGA | AGO | 240 |
| Val<br>65 | Lys | Thr | Ile | Ser | Glu<br>70 | Thr | Leu | Asn | Lys | Glu<br>75 | Tyr | Lys | Phe | Gly | Arg<br>80 | |
| AAT | TCG | AAA | ACT | GCG | TTA | AAA | AAG | TAT | CTT | GAT | TAT | GGT | AAA | GAG | GAG | 288 |
| Asn | Ser | Lys | Thr | Ala<br>85 | Leu | Lys | Lys | Tyr | Leu<br>90 | Asp | Tyr | Gly | Lys | Glu<br>95 | Glu | |
| TAT | TTG | ATT | CAA | TTT | TTT | AAT | ACC | CTT | ATG | CTA | GAA | AAC | AAT | ACA | TAT | 336 |
| Tyr | Leu | Ile | Gln<br>100 | Phe | Phe | Asn | Thr | Leu<br>105 | Met | Leu | Glu | Asn | Asn<br>110 | Thr | Tyr | |
| ATA | GAT | AGA | GAG | TAT | ATT | GAA | AGT | GTG | CTG | GCT | TTT | TGT | GAA | CCT | GTT | 384 |
| Ile | Asp | Arg<br>115 | Glu | Tyr | Ile | Glu | Ser<br>120 | Val | Leu | Ala | Phe | Cys<br>125 | Glu | Pro | Val | |
| TCA | AAA | GAA | AAA | ATT | AAA | AAT | GAG | TTT | ATA | AAG | CTT | TGG | AAT | GAA | GCT | 432 |
| Ser | Lys<br>130 | Glu | Lys | Ile | Lys | Asn<br>135 | Glu | Phe | Ile | Lys | Leu<br>140 | Trp | Asn | Glu | Ala | |
| AAT | GAA | GTT | AAT | GAA | TAC | GGT | AAG | TTA | AAG | GAT | TAC | TTA | TTG | GGA | ATT | 480 |
| Asn<br>145 | Glu | Val | Asn | Glu | Tyr<br>150 | Gly | Lys | Leu | Lys | Asp<br>155 | Tyr | Leu | Leu | Gly | Ile<br>160 | |
| TAT | TCA | AAG | CTA | TTC | TCA | ATG | GGA | CTA | GAA | AAT | TTA | AGA | CTA | ATA | GAA | 528 |
| Tyr | Ser | Lys | Leu | Phe<br>165 | Ser | Met | Gly | Leu | Glu<br>170 | Asn | Leu | Arg | Leu | Ile<br>175 | Glu | |
| ATT | TAT | AAT | TCT | AAT | GAA | AGC | CTT | ATA | AAA | AAG | GTA | TTT | AAA | TAC | GAG | 576 |
| Ile | Tyr | Asn | Ser<br>180 | Asn | Glu | Ser | Leu | Ile<br>185 | Lys | Lys | Val | Phe | Lys<br>190 | Tyr | Glu | |
| TCA | ACG | ATA | AAG | GAG | TTA | AAG | GAG | TAC | TGC | TTA | TCT | AAT | CAA | GAG | TCA | 624 |
| Ser | Thr | Ile<br>195 | Lys | Glu | Leu | Lys | Glu<br>200 | Tyr | Cys | Leu | Ser | Asn<br>205 | Gln | Glu | Ser | |
| ATT | ACT | GCT | GGT | TTA | GCC | ATC | AAG | ATG | TTT | AAT | GAA | AAG | TAT | ATG | GAA | 672 |
| Ile | Thr | Ala | Gly | Leu<br>210 | Ala | Ile | Lys | Met | Phe<br>215 | Asn | Glu | Lys | Tyr<br>220 | Met | Glu | |
| TTA | ATG | AAA | AAA | GAA | TAT | CAA | CAA | GAT | GCT | ATA | GCC | TTA | AAA | CTT | GAG | 720 |
| Leu | Met | Lys<br>225 | Lys | Glu | Tyr | Gln<br>230 | Gln | Asp | Ala | Ile<br>235 | Ala | Leu | Lys | Leu | Glu<br>240 | |
| GAG | CAT | ATG | AAT | CAA | TTG | TAT | GTT | GAT | AAT | AAT | ATT | AAT | GAA | TAT | CCT | 768 |
| Glu | His | Met | Asn | Gln<br>245 | Leu | Tyr | Val | Asp | Asn<br>250 | Asn | Ile | Asn | Glu | Tyr<br>255 | Pro | |
| TAT | ATT | TTT | GAC | CGG | GGA | AAT | GAT | ATT | CTA | CTC | TTA | CCT | ACA | GAA | GAG | 816 |
| Tyr | Ile | Phe | Asp | Arg<br>260 | Gly | Asn | Asp | Ile | Leu<br>265 | Leu | Leu | Pro | Thr | Glu<br>270 | Glu | |
| TAT | GAC | TTT | GTT | TAT | TTC | CAT | ATA | GAT | CAG | GAT | TTT | TTT | AAT | AGA | TTC | 864 |
| Tyr | Asp | Phe | Val<br>275 | Tyr | Phe | His | Ile | Asp<br>280 | Gln | Asp | Phe | Phe | Asn<br>285 | Arg | Phe | |
| CAA | GAT | GAA | AAT | AAA | TTC | TTG | GAT | TAT | GTA | CTT | TCG | TCC | ATA | AAA | CAA | 912 |
| Gln | Asp | Glu | Asn<br>290 | Lys | Phe | Leu | Asp | Tyr<br>295 | Val | Leu | Ser | Ser | Ile<br>300 | Lys | Gln | |
| ATT | TAT | CGT | GTG | TTA | GCT | AAT | GAA | AAA | GTT | TTT | GCG | TTG | AAG | ATT | GAT | 960 |
| Ile | Tyr | Arg<br>305 | Val | Leu | Ala | Asn | Glu<br>310 | Lys | Val | Phe | Ala | Leu<br>315 | Lys | Ile | Asp<br>320 | |
| AAT | ATT | TAC | AAT | AAT | GAA | AAA | AAT | TTG | AAA | TGG | GAA | CTT | TAT | CCA | AAA | 1008 |
| Asn | Ile | Tyr | Asn<br>325 | Asn | Glu | Lys | Asn | Leu<br>330 | Lys | Trp | Glu | Leu | Tyr<br>335 | Pro | Lys | |

| | | | | | | | | | | | | | | | | |
|---|---|---|---|---|---|---|---|---|---|---|---|---|---|---|---|---|
| CTA | ACA | ATC | TAC | TCT | GAA | CAT | TTT | ATA | CAA | ACA | AAA | GAA | ACT | GCT | AGG | 1056 |
| Leu | Thr | Ile | Tyr | Ser | Glu | His | Phe | Ile | Gln | Thr | Lys | Glu | Thr | Ala | Arg | |
| | | | 340 | | | | | 345 | | | | | 350 | | | |
| TTT | TAT | AAA | GCA | TAC | GAT | ATA | GCT | AAA | GAT | TTG | CTT | AGT | AAA | CAC | GAA | 1104 |
| Phe | Tyr | Lys | Ala | Tyr | Asp | Ile | Ala | Lys | Asp | Leu | Leu | Ser | Lys | His | Glu | |
| | | 355 | | | | | 360 | | | | | 365 | | | | |
| TTT | AGG | CTA | TTA | GAG | AAT | GAT | TCA | GAG | AAA | AAT | AGA | GAA | AAT | ATT | TTA | 1152 |
| Phe | Arg | Leu | Leu | Glu | Asn | Asp | Ser | Glu | Lys | Asn | Arg | Glu | Asn | Ile | Leu | |
| 370 | | | | | 375 | | | | | 380 | | | | | | |
| AAA | GAG | TAT | TTT | TCT | GGA | AAA | ATA | AGT | GAA | GAT | GAG | TTA | TTT | TCT | TTA | 1200 |
| Lys | Glu | Tyr | Phe | Ser | Gly | Lys | Ile | Ser | Glu | Asp | Glu | Leu | Phe | Ser | Leu | |
| 385 | | | | | 390 | | | | | 395 | | | | | 400 | |
| GTT | CAT | GTA | AAT | ATG | AAA | AAA | GAA | CAT | TTC | TTT | GAA | TTT | CTA | AAC | AGA | 1248 |
| Val | His | Val | Asn | Met | Lys | Lys | Glu | His | Phe | Phe | Glu | Phe | Leu | Asn | Arg | |
| | | | | 405 | | | | | 410 | | | | | 415 | | |
| TTT | AAA | TAT | GTA | CAT | TAT | GGT | TTT | ACA | TTT | AAT | GAT | TGT | CTA | GTG | TTA | 1296 |
| Phe | Lys | Tyr | Val | His | Tyr | Gly | Phe | Thr | Phe | Asn | Asp | Cys | Leu | Val | Leu | |
| | | | 420 | | | | | 425 | | | | | 430 | | | |
| GAC | AGG | GTT | GAT | AAA | AGC | TTT | GCA | AAT | GGT | GAG | CTA | GAA | AAT | GTC | ATA | 1344 |
| Asp | Arg | Val | Asp | Lys | Ser | Phe | Ala | Asn | Gly | Glu | Leu | Glu | Asn | Val | Ile | |
| | | 435 | | | | | 440 | | | | | 445 | | | | |
| AGT | AAT | GCA | ACA | GAA | ATA | CTT | CTT | ATT | TTC | TAT | AAG | TTT | AGA | GCG | GAT | 1392 |
| Ser | Asn | Ala | Thr | Glu | Ile | Leu | Leu | Ile | Phe | Tyr | Lys | Phe | Arg | Ala | Asp | |
| 450 | | | | | 455 | | | | | 460 | | | | | | |
| CAA | AGG | AGA | ATT | CCT | TGT | CCT | TCT | TGT | GGT | AGT | TTG | AAT | ATT | TCT | GGG | 1440 |
| Gln | Arg | Arg | Ile | Pro | Cys | Pro | Ser | Cys | Gly | Ser | Leu | Asn | Ile | Ser | Gly | |
| 465 | | | | | 470 | | | | | 475 | | | | | 480 | |
| AAC | TCT | TAC | CCA | GAA | ATA | AAT | AAT | AGA | AGC | TGG | GAA | TGT | AAA | TCT | CCT | 1488 |
| Asn | Ser | Tyr | Pro | Glu | Ile | Asn | Asn | Arg | Ser | Trp | Glu | Cys | Lys | Ser | Pro | |
| | | | | 485 | | | | | 490 | | | | | 495 | | |
| TAT | TGT | CCA | GAC | AGG | AGT | AAA | TCT | AAT | CGT | GGT | AAA | CGA | TAT | TCT | AAA | 1536 |
| Tyr | Cys | Pro | Asp | Arg | Ser | Lys | Ser | Asn | Arg | Gly | Lys | Arg | Tyr | Ser | Lys | |
| | | | 500 | | | | | 505 | | | | | 510 | | | |
| AAA | TCT | AAT | TAT | ATG | CAA | TGG | GGA | GCT | ATT | TAT | CCA | AAA | TCT | CAT | GAC | 1584 |
| Lys | Ser | Asn | Tyr | Met | Gln | Trp | Gly | Ala | Ile | Tyr | Pro | Lys | Ser | His | Asp | |
| | | 515 | | | | | 520 | | | | | 525 | | | | |
| ATC | ATT | CCT | CGA | GAA | TTA | ATT | AAA | AAG | TGG | AGA | AGA | GAT | ATA | ATT | GTA | 1632 |
| Ile | Ile | Pro | Arg | Glu | Leu | Ile | Lys | Lys | Trp | Arg | Arg | Asp | Ile | Ile | Val | |
| 530 | | | | | 535 | | | | | 540 | | | | | | |
| ATT | AAT | AAT | GAA | CAA | GAA | ATC | TTT | GAG | ATG | CTT | GTG | AAA | TAC | TTT | AGT | 1680 |
| Ile | Asn | Asn | Glu | Gln | Glu | Ile | Phe | Glu | Met | Leu | Val | Lys | Tyr | Phe | Ser | |
| 545 | | | | | 550 | | | | | 555 | | | | | 560 | |
| TTC | ACA | GAT | GAA | AAA | TTG | TTA | TTT | ATC | AAT | ACG | AAT | GAA | CTA | CCT | AGT | 1728 |
| Phe | Thr | Asp | Glu | Lys | Leu | Leu | Phe | Ile | Asn | Thr | Asn | Glu | Leu | Pro | Ser | |
| | | | | 565 | | | | | 570 | | | | | 575 | | |
| GTA | GTT | ACA | GAA | CGT | GAA | AAT | AGA | AAG | GTT | GTT | ATA | TTA | TCT | CAA | AAG | 1776 |
| Val | Val | Thr | Glu | Arg | Glu | Asn | Arg | Lys | Val | Val | Ile | Leu | Ser | Gln | Lys | |
| | | | 580 | | | | | 585 | | | | | 590 | | | |
| CTG | AAA | GAA | AAA | GCA | TAT | ACA | AGT | AAT | GTA | GTT | GTA | AAG | GAA | AGC | TTA | 1824 |
| Leu | Lys | Glu | Lys | Ala | Tyr | Thr | Ser | Asn | Val | Val | Val | Lys | Glu | Ser | Leu | |
| | | | | 595 | | | | | 600 | | | | | 605 | | |
| GAA | GGA | GAA | ATA | GAG | TTT | TTC | AAG | AAC | GGT | TTA | TAT | CTC | AAG | AAT | TTT | 1872 |
| Glu | Gly | Glu | Ile | Glu | Phe | Phe | Lys | Asn | Gly | Leu | Tyr | Leu | Lys | Asn | Phe | |
| | | | 610 | | | | | 615 | | | | | 620 | | | |
| ACT | GAG | TTG | TAT | TTA | CCA | GAG | GAT | CAA | AGA | AGA | GTC | TCT | CCT | GAA | ATA | 1920 |
| Thr | Glu | Leu | Tyr | Leu | Pro | Glu | Asp | Gln | Arg | Arg | Val | Ser | Pro | Glu | Ile | |
| 625 | | | | | 630 | | | | | 635 | | | | | 640 | |
| AAT | AAC | TTT | TTA | AAT | AGT | GGG | GGA | CGG | TTA | AAA | TTA | ATA | CAA | GGA | GAT | 19 |
| Asn | Asn | Phe | Leu | Asn | Ser | Gly | Gly | Arg | Leu | Lys | Leu | Ile | Gln | Gly | Asp | |
| | | | | 645 | | | | | 650 | | | | | 655 | | |

```
AGT  TAC  GAA  GTA  TTA  AAA  AGT  GTA  GAA  GAT  AAT  ACT  TTT  GCA  GCA  GCA       20
Ser  Tyr  Glu  Val  Leu  Lys  Ser  Val  Glu  Asp  Asn  Thr  Phe  Ala  Ala  Ala
               660                 665                      670

GTG  ACT  TCG  CCT  CCA  TAC  TAC  AAT  GCT  AGG  GAA  TAT  TCT  CAA  TGG  CCG       20
Val  Thr  Ser  Pro  Pro  Tyr  Tyr  Asn  Ala  Arg  Glu  Tyr  Ser  Gln  Trp  Pro
          675                      680                      685

AAC  CTA  TAT  TTA  TAC  TTT  AAT  GAT  ATG  TAT  AAC  ATT  ATT  AAA  GAA  TGC       21
Asn  Leu  Tyr  Leu  Tyr  Phe  Asn  Asp  Met  Tyr  Asn  Ile  Ile  Lys  Glu  Cys
     690                      695                      700

TTT  AGA  ACT  CTA  AAA  CCG  GGT  AGT  GTA  TTC  CTT  TAT  AAC  ATT  GCT  GAT       21
Phe  Arg  Thr  Leu  Lys  Pro  Gly  Ser  Val  Phe  Leu  Tyr  Asn  Ile  Ala  Asp
705                      710                      715                      720

ATC  GTT  GAC  AAT  GAA  AAT  ATA  ATA  GTC  AAA  TCA  TCA  ATG  GGA  AAT  AAA       22
Ile  Val  Asp  Asn  Glu  Asn  Ile  Ile  Val  Lys  Ser  Ser  Met  Gly  Asn  Lys
               725                      730                      735

AGA  ATC  CCT  CTT  GGT  GCA  TAT  ACT  ATT  TAT  TTC  TTC  CAA  AAG  GCA  GGT       22
Arg  Ile  Pro  Leu  Gly  Ala  Tyr  Thr  Ile  Tyr  Phe  Phe  Gln  Lys  Ala  Gly
          740                      745                      750

TTT  GAG  CTA  CTA  GAT  AAT  ATT  ATA  TGG  GAT  AAA  GGC  GAG  CCA  CAA  AGT       23
Phe  Glu  Leu  Leu  Asp  Asn  Ile  Ile  Trp  Asp  Lys  Gly  Glu  Pro  Gln  Ser
          755                      760                      765

AAT  AGG  CAA  AAA  AAT  GAT  GGT  AAG  TTT  ACA  CCT  CAC  TAT  CAA  AAG  CCA       23
Asn  Arg  Gln  Lys  Asn  Asp  Gly  Lys  Phe  Thr  Pro  His  Tyr  Gln  Lys  Pro
     770                      775                      780

CTA  AAT  GCT  TAT  GAG  CAT  ATG  TTT  ATT  TTT  AAA  AAG  ACA  GGC  GCT  CCT       24
Leu  Asn  Ala  Tyr  Glu  His  Met  Phe  Ile  Phe  Lys  Lys  Thr  Gly  Ala  Pro
785                      790                      795                      800

TTA  ACT  TTA  AGT  GAC  GAT  TGG  CAA  AGT  AAA  CGA  GGA  AGC  TGG  ATT  AAA       24
Leu  Thr  Leu  Ser  Asp  Asp  Trp  Gln  Ser  Lys  Arg  Gly  Ser  Trp  Ile  Lys
               805                      810                      815

AAT  ATA  GTA  CCT  TTT  CAG  CCT  GTT  TTT  AAG  ATA  AAT  TCA  AAA  GGT  GAA       24
Asn  Ile  Val  Pro  Phe  Gln  Pro  Val  Phe  Lys  Ile  Asn  Ser  Lys  Gly  Glu
          820                      825                      830

AAT  ATC  TTA  GGT  CAC  ACA  GCA  CCA  TTC  CCT  GAA  GAC  ATT  CCA  AGA  TTT       25
Asn  Ile  Leu  Gly  His  Thr  Ala  Pro  Phe  Pro  Glu  Asp  Ile  Pro  Arg  Phe
          835                      840                      845

GTT  GCT  AAT  GTG  TTT  ACA  AAA  CAT  GAT  AAT  GAT  ATA  ATA  TTA  GAT  CCA       25
Val  Ala  Asn  Val  Phe  Thr  Lys  His  Asp  Asn  Asp  Ile  Ile  Leu  Asp  Pro
850                      855                      860

TTT  TCA  GGC  TCA  TTA  ACT  TCA  GCT  ATA  GCT  TCG  TAT  AAA  AGC  AAT  AGA       26
Phe  Ser  Gly  Ser  Leu  Thr  Ser  Ala  Ile  Ala  Ser  Tyr  Lys  Ser  Asn  Arg
865                      870                      875                      880

ATA  GGT  CTT  GGA  ATT  GAG  TTG  TCT  CCT  GAT  TAT  GTT  GAA  TTA  TCT  AGG       26
Ile  Gly  Leu  Gly  Ile  Glu  Leu  Ser  Pro  Asp  Tyr  Val  Glu  Leu  Ser  Arg
               885                      890                      895

GAC  AGA  GCG  TTA  TTA  GAA  GGG  GTA  ACT  ACT  AAA  ATT  TTA  AAT  TTT  AAT       27
Asp  Arg  Ala  Leu  Leu  Glu  Gly  Val  Thr  Thr  Lys  Ile  Leu  Asn  Phe  Asn
               900                      905                      910

TAA                                                                                   27
```

( 2 ) INFORMATION FOR SEQ ID NO:2:

( i ) SEQUENCE CHARACTERISTICS:
        ( A ) LENGTH: 912 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

-continued

```
Met  Asn  Trp  Ile  Phe  Asn  Thr  Leu  Ile  Gln  Phe  Leu  Glu  Asp  Leu  Asn
 1              5                   10                            15

Ile  Asp  Pro  Ser  Val  Val  Ser  Leu  Ile  Asp  Glu  Asp  Ala  Lys  Lys  Leu
               20                   25                       30

Glu  Glu  Gln  Phe  Pro  Lys  Ala  Leu  Lys  His  Pro  Val  Val  Asp  Glu  Glu
          35                   40                       45

Ile  Val  Tyr  Lys  Ile  Leu  Cys  Glu  Lys  Tyr  Asn  Leu  Asn  Ala  Leu  Asn
     50                   55                        60

Val  Lys  Thr  Ile  Ser  Glu  Thr  Leu  Asn  Lys  Glu  Tyr  Lys  Phe  Gly  Arg
 65                       70                   75                            80

Asn  Ser  Lys  Thr  Ala  Leu  Lys  Lys  Tyr  Leu  Asp  Tyr  Gly  Lys  Glu  Glu
               85                   90                        95

Tyr  Leu  Ile  Gln  Phe  Phe  Asn  Thr  Leu  Met  Leu  Glu  Asn  Asn  Thr  Tyr
          100                  105                      110

Ile  Asp  Arg  Glu  Tyr  Ile  Glu  Ser  Val  Leu  Ala  Phe  Cys  Glu  Pro  Val
          115                  120                      125

Ser  Lys  Glu  Lys  Ile  Lys  Asn  Glu  Phe  Ile  Lys  Leu  Trp  Asn  Glu  Ala
     130                  135                      140

Asn  Glu  Val  Asn  Glu  Tyr  Gly  Lys  Leu  Lys  Asp  Tyr  Leu  Leu  Gly  Ile
145                       150                  155                           160

Tyr  Ser  Lys  Leu  Phe  Ser  Met  Gly  Leu  Glu  Asn  Leu  Arg  Leu  Ile  Glu
                    165                  170                       175

Ile  Tyr  Asn  Ser  Asn  Glu  Ser  Leu  Ile  Lys  Lys  Val  Phe  Lys  Tyr  Glu
               180                  185                       190

Ser  Thr  Ile  Lys  Glu  Leu  Lys  Glu  Tyr  Cys  Leu  Ser  Asn  Gln  Glu  Ser
          195                  200                      205

Ile  Thr  Ala  Gly  Leu  Ala  Ile  Lys  Met  Phe  Asn  Glu  Lys  Tyr  Met  Glu
     210                  215                      220

Leu  Met  Lys  Lys  Glu  Tyr  Gln  Gln  Asp  Ala  Ile  Ala  Leu  Lys  Leu  Glu
225                       230                  235                           240

Glu  His  Met  Asn  Gln  Leu  Tyr  Val  Asp  Asn  Asn  Ile  Asn  Glu  Tyr  Pro
                    245                  250                       255

Tyr  Ile  Phe  Asp  Arg  Gly  Asn  Asp  Ile  Leu  Leu  Leu  Pro  Thr  Glu  Glu
               260                  265                       270

Tyr  Asp  Phe  Val  Tyr  Phe  His  Ile  Asp  Gln  Asp  Phe  Phe  Asn  Arg  Phe
          275                  280                      285

Gln  Asp  Glu  Asn  Lys  Phe  Leu  Asp  Tyr  Val  Leu  Ser  Ser  Ile  Lys  Gln
     290                  295                      300

Ile  Tyr  Arg  Val  Leu  Ala  Asn  Glu  Lys  Val  Phe  Ala  Leu  Lys  Ile  Asp
305                       310                  315                           320

Asn  Ile  Tyr  Asn  Asn  Glu  Lys  Asn  Leu  Lys  Trp  Glu  Leu  Tyr  Pro  Lys
                    325                  330                       335

Leu  Thr  Ile  Tyr  Ser  Glu  His  Phe  Ile  Gln  Thr  Lys  Glu  Thr  Ala  Arg
                    340                  345                       350

Phe  Tyr  Lys  Ala  Tyr  Asp  Ile  Ala  Lys  Asp  Leu  Leu  Ser  Lys  His  Glu
          355                  360                      365

Phe  Arg  Leu  Leu  Glu  Asn  Asp  Ser  Glu  Lys  Asn  Arg  Glu  Asn  Ile  Leu
     370                  375                      380

Lys  Glu  Tyr  Phe  Ser  Gly  Lys  Ile  Ser  Glu  Asp  Glu  Leu  Phe  Ser  Leu
385                       390                  395                           400

Val  His  Val  Asn  Met  Lys  Lys  Glu  His  Phe  Phe  Glu  Phe  Leu  Asn  Arg
                    405                  410                       415

Phe  Lys  Tyr  Val  His  Tyr  Gly  Phe  Thr  Phe  Asn  Asp  Cys  Leu  Val  Leu
```

```
                          420                        425                        430
Asp  Arg  Val  Asp  Lys  Ser  Phe  Ala  Asn  Gly  Glu  Leu  Glu  Asn  Val  Ile
               435                        440                        445

Ser  Asn  Ala  Thr  Glu  Ile  Leu  Leu  Ile  Phe  Tyr  Lys  Phe  Arg  Ala  Asp
     450                        455                        460

Gln  Arg  Arg  Ile  Pro  Cys  Pro  Ser  Cys  Gly  Ser  Leu  Asn  Ile  Ser  Gly
465                       470                        475                       480

Asn  Ser  Tyr  Pro  Glu  Ile  Asn  Asn  Arg  Ser  Trp  Glu  Cys  Lys  Ser  Pro
                    485                        490                       495

Tyr  Cys  Pro  Asp  Arg  Ser  Lys  Ser  Asn  Arg  Gly  Lys  Arg  Tyr  Ser  Lys
               500                        505                        510

Lys  Ser  Asn  Tyr  Met  Gln  Trp  Gly  Ala  Ile  Tyr  Pro  Lys  Ser  His  Asp
          515                        520                        525

Ile  Ile  Pro  Arg  Glu  Leu  Ile  Lys  Lys  Trp  Arg  Arg  Asp  Ile  Ile  Val
          530                        535                        540

Ile  Asn  Asn  Glu  Gln  Glu  Ile  Phe  Glu  Met  Leu  Val  Lys  Tyr  Phe  Ser
545                       550                        555                       560

Phe  Thr  Asp  Glu  Lys  Leu  Leu  Phe  Ile  Asn  Thr  Asn  Glu  Leu  Pro  Ser
                    565                        570                       575

Val  Val  Thr  Glu  Arg  Glu  Asn  Arg  Lys  Val  Val  Ile  Leu  Ser  Gln  Lys
               580                        585                        590

Leu  Lys  Glu  Lys  Ala  Tyr  Thr  Ser  Asn  Val  Val  Val  Lys  Glu  Ser  Leu
          595                        600                        605

Glu  Gly  Glu  Ile  Glu  Phe  Phe  Lys  Asn  Gly  Leu  Tyr  Leu  Lys  Asn  Phe
          610                        615                        620

Thr  Glu  Leu  Tyr  Leu  Pro  Glu  Asp  Gln  Arg  Arg  Val  Ser  Pro  Glu  Ile
625                       630                        635                       640

Asn  Asn  Phe  Leu  Asn  Ser  Gly  Gly  Arg  Leu  Lys  Leu  Ile  Gln  Gly  Asp
                    645                        650                       655

Ser  Tyr  Glu  Val  Leu  Lys  Ser  Val  Glu  Asp  Asn  Thr  Phe  Ala  Ala  Ala
               660                        665                        670

Val  Thr  Ser  Pro  Pro  Tyr  Tyr  Asn  Ala  Arg  Glu  Tyr  Ser  Gln  Trp  Pro
          675                        680                        685

Asn  Leu  Tyr  Leu  Tyr  Phe  Asn  Asp  Met  Tyr  Asn  Ile  Ile  Lys  Glu  Cys
     690                        695                        700

Phe  Arg  Thr  Leu  Lys  Pro  Gly  Ser  Val  Phe  Leu  Tyr  Asn  Ile  Ala  Asp
705                       710                        715                       720

Ile  Val  Asp  Asn  Glu  Asn  Ile  Ile  Val  Lys  Ser  Ser  Met  Gly  Asn  Lys
                    725                        730                       735

Arg  Ile  Pro  Leu  Gly  Ala  Tyr  Thr  Ile  Tyr  Phe  Phe  Gln  Lys  Ala  Gly
               740                        745                        750

Phe  Glu  Leu  Leu  Asp  Asn  Ile  Ile  Trp  Asp  Lys  Gly  Glu  Pro  Gln  Ser
          755                        760                        765

Asn  Arg  Gln  Lys  Asn  Asp  Gly  Lys  Phe  Thr  Pro  His  Tyr  Gln  Lys  Pro
     770                        775                        780

Leu  Asn  Ala  Tyr  Glu  His  Met  Phe  Ile  Phe  Lys  Lys  Thr  Gly  Ala  Pro
785                       790                        795                       800

Leu  Thr  Leu  Ser  Asp  Asp  Trp  Gln  Ser  Lys  Arg  Gly  Ser  Trp  Ile  Lys
                    805                        810                       815

Asn  Ile  Val  Pro  Phe  Gln  Pro  Val  Phe  Lys  Ile  Asn  Ser  Lys  Gly  Glu
               820                        825                        830

Asn  Ile  Leu  Gly  His  Thr  Ala  Pro  Phe  Pro  Glu  Asp  Ile  Pro  Arg  Phe
          835                        840                        845
```

```
                    Val  Ala  Asn  Val  Phe  Thr  Lys  His  Asp  Asn  Asp  Ile  Ile  Leu  Asp  Pro
                                   850                      855                     860

Phe  Ser  Gly  Ser  Leu  Thr  Ser  Ala  Ile  Ala  Ser  Tyr  Lys  Ser  Asn  Arg
                    865                           870                     875                     880

Ile  Gly  Leu  Gly  Ile  Glu  Leu  Ser  Pro  Asp  Tyr  Val  Glu  Leu  Ser  Arg
                                        885                          890                      895

Asp  Arg  Ala  Leu  Leu  Glu  Gly  Val  Thr  Thr  Lys  Ile  Leu  Asn  Phe  Asn
                                   900                      905                     910
```

( 2 ) INFORMATION FOR SEQ ID NO:3:

( i ) SEQUENCE CHARACTERISTICS:
        ( A ) LENGTH: 678 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: Coding Sequence
        ( B ) LOCATION: 1...675
        ( D ) OTHER INFORMATION:

( x i ) SEQUENCE DESCRIPTION: SEQ ID NO:3:

```
ATG  GAA  CGT  CAA  TTA  AAA  TCA  ATT  GCT  TAC  GCT  TTT  GTT  GCA  AAC  GAT         48
Met  Glu  Arg  Gln  Leu  Lys  Ser  Ile  Ala  Tyr  Ala  Phe  Val  Ala  Asn  Asp
1                        5                        10                       15

ATA  GAT  GTG  TAT  ATA  CCA  GAT  GGA  GAA  TCA  AAT  TGT  ATA  GTG  GTA  ACC         96
Ile  Asp  Val  Tyr  Ile  Pro  Asp  Gly  Glu  Ser  Asn  Cys  Ile  Val  Val  Thr
                    20                       25                       30

AAA  TTG  GTT  TGC  AAG  GAT  TGC  GGG  CAA  TAT  TGG  CAT  ACT  AGC  TTA  TCA        144
Lys  Leu  Val  Cys  Lys  Asp  Cys  Gly  Gln  Tyr  Trp  His  Thr  Ser  Leu  Ser
               35                       40                       45

GAG  TGT  TAT  TTT  TGT  GGT  ACT  TTG  AAT  TTT  TAT  CTA  TAT  GAA  TGT  AAT        192
Glu  Cys  Tyr  Phe  Cys  Gly  Thr  Leu  Asn  Phe  Tyr  Leu  Tyr  Glu  Cys  Asn
          50                       55                       60

TCT  TGT  GGA  AAA  AAA  TAT  TCA  TTA  ACT  TCT  TCT  TCA  AAA  TCT  TGT  GAT        240
Ser  Cys  Gly  Lys  Lys  Tyr  Ser  Leu  Thr  Ser  Ser  Ser  Lys  Ser  Cys  Asp
65                       70                       75                       80

ACT  GAT  GGT  TGT  AAT  GGT  AAA  TTA  ATC  AAA  AGA  TGT  AGC  AAT  CCA  GAA        28
Thr  Asp  Gly  Cys  Asn  Gly  Lys  Leu  Ile  Lys  Arg  Cys  Ser  Asn  Pro  Glu
                    85                       90                       95

TGT  ATT  AGT  CGG  ACA  AAT  GAA  GAA  ATA  CAG  CGT  GCA  ACA  GAT  GAG  CAA        33
Cys  Ile  Ser  Arg  Thr  Asn  Glu  Glu  Ile  Gln  Arg  Ala  Thr  Asp  Glu  Gln
               100                      105                      110

GGA  GGA  GTA  TTT  GAT  CTC  AAT  TCA  TCT  TTT  AAC  GTA  TCT  TTA  AAT  CAT        38
Gly  Gly  Val  Phe  Asp  Leu  Asn  Ser  Ser  Phe  Asn  Val  Ser  Leu  Asn  His
          115                      120                      125

TGT  GTG  ACA  TGT  GGA  AGT  AAA  GAA  AAC  TAT  TAC  AAA  ACA  TAT  CGT  ATA        43
Cys  Val  Thr  Cys  Gly  Ser  Lys  Glu  Asn  Tyr  Tyr  Lys  Thr  Tyr  Arg  Ile
     130                      135                      140

TAC  TCT  TAT  CGA  ACG  GAA  GTA  GAA  CCA  AAT  ATA  GAA  GCT  TTA  AGA  GAG        48
Tyr  Ser  Tyr  Arg  Thr  Glu  Val  Glu  Pro  Asn  Ile  Glu  Ala  Leu  Arg  Glu
145                      150                      155                      160

TTT  GCC  AAT  AAC  AAC  AAA  CTT  AAT  AGT  GAT  GAA  GAT  GTT  ATA  ATC  ATT        52
Phe  Ala  Asn  Asn  Asn  Lys  Leu  Asn  Ser  Asp  Glu  Asp  Val  Ile  Ile  Ile
                    165                      170                      175

AAA  CAC  CTA  GTT  GAT  AAT  GTA  ATT  CAT  TAC  GGT  TAT  ATT  CCA  TAC  AGT        57
Lys  His  Leu  Val  Asp  Asn  Val  Ile  His  Tyr  Gly  Tyr  Ile  Pro  Tyr  Ser
               180                      185                      190

AAG  TTA  GAT  GAA  ACA  ACA  GAA  ATT  ACT  ACA  ACA  TTT  TCT  CGT  TTT  TCT        62
Lys  Leu  Asp  Glu  Thr  Thr  Glu  Ile  Thr  Thr  Thr  Phe  Ser  Arg  Phe  Ser
```

```
                          195                    200                         205
GAT CTT GTT TCA GAA TTG TTC CCA GTT AAC GTT CCT CCA AAT GTT ACT                  67
Asp Leu Val Ser Glu Leu Phe Pro Val Asn Val Pro Pro Asn Val Thr
    210                    215                   220

GAA TAA                                                                          67
Glu
225
```

(2) INFORMATION FOR SEQ ID NO:4:

(i) SEQUENCE CHARACTERISTICS:
        (A) LENGTH: 225 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Glu Arg Gln Leu Lys Ser Ile Ala Tyr Ala Phe Val Ala Asn Asp
1               5                   10                  15

Ile Asp Val Tyr Ile Pro Asp Gly Glu Ser Asn Cys Ile Val Val Thr
            20                  25                  30

Lys Leu Val Cys Lys Asp Cys Gly Gln Tyr Trp His Thr Ser Leu Ser
            35                  40                  45

Glu Cys Tyr Phe Cys Gly Thr Leu Asn Phe Tyr Leu Tyr Glu Cys Asn
        50                  55                  60

Ser Cys Gly Lys Lys Tyr Ser Leu Thr Ser Ser Lys Ser Cys Asp
65                  70                  75                  80

Thr Asp Gly Cys Asn Gly Lys Leu Ile Lys Arg Cys Ser Asn Pro Glu
                85                  90                  95

Cys Ile Ser Arg Thr Asn Glu Glu Ile Gln Arg Ala Thr Asp Glu Gln
            100                 105                 110

Gly Gly Val Phe Asp Leu Asn Ser Ser Phe Asn Val Ser Leu Asn His
            115                 120                 125

Cys Val Thr Cys Gly Ser Lys Glu Asn Tyr Tyr Lys Thr Tyr Arg Ile
        130                 135                 140

Tyr Ser Tyr Arg Thr Glu Val Glu Pro Asn Ile Glu Ala Leu Arg Glu
145                 150                 155                 160

Phe Ala Asn Asn Asn Lys Leu Asn Ser Asp Glu Asp Val Ile Ile Ile
                165                 170                 175

Lys His Leu Val Asp Asn Val Ile His Tyr Gly Tyr Ile Pro Tyr Ser
            180                 185                 190

Lys Leu Asp Glu Thr Thr Glu Ile Thr Thr Thr Phe Ser Arg Phe Ser
            195                 200                 205

Asp Leu Val Ser Glu Leu Phe Pro Val Asn Val Pro Pro Asn Val Thr
        210                 215                 220

Glu
225
```

(2) INFORMATION FOR SEQ ID NO:5:

(i) SEQUENCE CHARACTERISTICS:
        (A) LENGTH: 906 base pairs
        (B) TYPE: nucleic acid
        (C) STRANDEDNESS: single
        (D) TOPOLOGY: linear (  i i  ) MOLECULE TYPE: Genomic DNA (  i x  ) FEATURE:
    ( A ) NAME/KEY: Coding Sequence
    ( B ) LOCATION: 1...903
    ( D ) OTHER INFORMATION:

(  x i  ) SEQUENCE DESCRIPTION: SEQ ID NO:5:

```
ATG  GAA  CAA  CAA  AAA  TTC  CCT  AAT  CCA  AGA  ATT  TTT  GAG  GAT  ATT  GAT         4 8
Met  Glu  Gln  Gln  Lys  Phe  Pro  Asn  Pro  Arg  Ile  Phe  Glu  Asp  Ile  Asp
 1                  5                       1 0                      1 5

GCA  ACT  GAT  TTT  TCA  AAA  CAT  AAT  AAA  AAG  CAT  GTA  ACA  GAG  GAC  TTT         9 6
Ala  Thr  Asp  Phe  Ser  Lys  His  Asn  Lys  Lys  His  Val  Thr  Glu  Asp  Phe
               2 0                      2 5                      3 0

GTG  GCT  GAA  AAC  TTT  AAA  GAT  GTT  GGT  TGG  AGA  GTT  TAT  CGT  CCT  TTT       1 4 4
Val  Ala  Glu  Asn  Phe  Lys  Asp  Val  Gly  Trp  Arg  Val  Tyr  Arg  Pro  Phe
          3 5                      4 0                      4 5

AAC  GAT  ACA  GGA  ATT  GAT  CTT  ATT  GCC  AAG  AAA  TTT  GTA  TGT  CCT  GAT       1 9 2
Asn  Asp  Thr  Gly  Ile  Asp  Leu  Ile  Ala  Lys  Lys  Phe  Val  Cys  Pro  Asp
     5 0                      5 5                      6 0

GGA  CAT  ACA  AAG  TGG  AAT  CAA  AAT  CTA  ACA  AAA  GAA  ATG  ACT  TGT  AGT       2 4
Gly  His  Thr  Lys  Trp  Asn  Gln  Asn  Leu  Thr  Lys  Glu  Met  Thr  Cys  Ser
6 5                 7 0                      7 5                      8 0

GAA  TGC  GGA  AAA  TCA  TTA  ATT  GAA  ATA  ACA  CGT  TTT  ATT  CAA  GTA  AAA       2 8
Glu  Cys  Gly  Lys  Ser  Leu  Ile  Glu  Ile  Thr  Arg  Phe  Ile  Gln  Val  Lys
                    8 5                      9 0                      9 5

ACT  CGG  GAA  GTT  AAA  CAA  GTA  AAA  ACT  CGG  GAA  GCT  AAA  GGA  GAA  AAG       3 3
Thr  Arg  Glu  Val  Lys  Gln  Val  Lys  Thr  Arg  Glu  Ala  Lys  Gly  Glu  Lys
               1 0 0                    1 0 5                    1 1 0

TTT  TTT  TTC  GGT  TAC  ACC  TTA  AAA  TCA  AAG  GAT  TTC  CGA  ACC  GAT  CCT       3 8
Phe  Phe  Phe  Gly  Tyr  Thr  Leu  Lys  Ser  Lys  Asp  Phe  Arg  Thr  Asp  Pro
          1 1 5                    1 2 0                    1 2 5

AGA  CAT  GTA  TTT  CTC  TTA  TAC  TCA  GAT  TTT  ACT  ATG  GAT  TTC  ATT  ATT       4 3
Arg  His  Val  Phe  Leu  Leu  Tyr  Ser  Asp  Phe  Thr  Met  Asp  Phe  Ile  Ile
     1 3 0                    1 3 5                    1 4 0

CTT  CCT  ATG  TAT  GAT  TAT  CTA  AAC  TTG  TTT  TAT  ACT  AAC  CAA  AGT  TTA       4 8
Leu  Pro  Met  Tyr  Asp  Tyr  Leu  Asn  Leu  Phe  Tyr  Thr  Asn  Gln  Ser  Leu
1 4 5               1 5 0                    1 5 5                    1 6 0

GGC  TCA  ACA  CAC  TTT  AGT  ACC  CCT  TCT  TTT  CGC  CAA  GGG  AAT  AAT  AAA       5 2
Gly  Ser  Thr  His  Phe  Ser  Thr  Pro  Ser  Phe  Arg  Gln  Gly  Asn  Asn  Lys
                    1 6 5                    1 7 0                    1 7 5

CTG  AAC  GGT  CTT  TCG  AAA  GAC  AAG  AAT  GAT  AAC  TGG  GTT  TGG  AGT  GGA       5 7
Leu  Asn  Gly  Leu  Ser  Lys  Asp  Lys  Asn  Asp  Asn  Trp  Val  Trp  Ser  Gly
               1 8 0                    1 8 5                    1 9 0

GTT  TCG  TTT  AAT  GAA  TTC  GTA  AAT  GAA  AAA  GGT  ATG  GAT  AAA  CTT  AGC       6 2
Val  Ser  Phe  Asn  Glu  Phe  Val  Asn  Glu  Lys  Gly  Met  Asp  Lys  Leu  Ser
          1 9 5                    2 0 0                    2 0 5

TGT  CCA  ATC  TAC  GAT  ATT  GAA  TTA  GAG  AGC  TAT  ACT  AAG  AAA  ATA  CAA       6 7
Cys  Pro  Ile  Tyr  Asp  Ile  Glu  Leu  Glu  Ser  Tyr  Thr  Lys  Lys  Ile  Gln
     2 1 0                    2 1 5                    2 2 0

GAA  TTA  AAA  TTT  AGC  TTA  TTC  TAT  CGG  TAC  TCT  CCT  GGT  AGA  AAA  AAT       7 2
Glu  Leu  Lys  Phe  Ser  Leu  Phe  Tyr  Arg  Tyr  Ser  Pro  Gly  Arg  Lys  Asn
2 2 5               2 3 0                    2 3 5                    2 4 0

CAG  GTA  TCA  GCT  CCT  ACT  GTC  GAA  TTT  ATT  AAT  AAT  CAT  TTT  AGC  ATT       7 6
Gln  Val  Ser  Ala  Pro  Thr  Val  Glu  Phe  Ile  Asn  Asn  His  Phe  Ser  Ile
                    2 4 5                    2 5 0                    2 5 5

TTT  ATA  AGT  CTA  CCA  AAG  GAA  GCT  ATT  GCT  AGC  AAA  AGG  AAG  GCA  CAT       8 1
Phe  Ile  Ser  Leu  Pro  Lys  Glu  Ala  Ile  Ala  Ser  Lys  Arg  Lys  Ala  His
               2 6 0                    2 6 5                    2 7 0

CTT  GAA  AGC  CTA  CGT  CAA  GAT  CTC  CCA  GAA  GAT  TTG  AAA  AAG  AGT  GTT       8 6
Leu  Glu  Ser  Leu  Arg  Gln  Asp  Leu  Pro  Glu  Asp  Leu  Lys  Lys  Ser  Val
          2 7 5                    2 8 0                    2 8 5
```

```
AAC  GAA  GGA  TAC  CTA  GTC  AAA  TTT  AAA  GGG  GTT  GAC  TTA  TAA                    90
Asn  Glu  Gly  Tyr  Leu  Val  Lys  Phe  Lys  Gly  Val  Asp  Leu
290                 295                      300
```

(2) INFORMATION FOR SEQ ID NO:6:

(i) SEQUENCE CHARACTERISTICS:
        (A) LENGTH: 301 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

```
Met  Glu  Gln  Gln  Lys  Phe  Pro  Asn  Pro  Arg  Ile  Phe  Glu  Asp  Ile  Asp
 1              5                    10                       15
Ala  Thr  Asp  Phe  Ser  Lys  His  Asn  Lys  His  Val  Thr  Glu  Asp  Phe
               20                  25                  30
Val  Ala  Glu  Asn  Phe  Lys  Asp  Val  Gly  Trp  Arg  Val  Tyr  Arg  Pro  Phe
          35                  40                  45
Asn  Asp  Thr  Gly  Ile  Asp  Leu  Ile  Ala  Lys  Lys  Phe  Val  Cys  Pro  Asp
     50                  55                  60
Gly  His  Thr  Lys  Trp  Asn  Gln  Asn  Leu  Thr  Lys  Glu  Met  Thr  Cys  Ser
65                  70                  75                       80
Glu  Cys  Gly  Lys  Ser  Leu  Ile  Glu  Ile  Thr  Arg  Phe  Ile  Gln  Val  Lys
               85                  90                  95
Thr  Arg  Glu  Val  Lys  Gln  Val  Lys  Thr  Arg  Glu  Ala  Lys  Gly  Glu  Lys
              100                 105                 110
Phe  Phe  Phe  Gly  Tyr  Thr  Leu  Lys  Ser  Lys  Asp  Phe  Arg  Thr  Asp  Pro
          115                 120                 125
Arg  His  Val  Phe  Leu  Leu  Tyr  Ser  Asp  Phe  Thr  Met  Asp  Phe  Ile  Ile
     130                 135                 140
Leu  Pro  Met  Tyr  Asp  Tyr  Leu  Asn  Leu  Phe  Tyr  Thr  Asn  Gln  Ser  Leu
145                 150                 155                      160
Gly  Ser  Thr  His  Phe  Ser  Thr  Pro  Ser  Phe  Arg  Gln  Gly  Asn  Asn  Lys
               165                 170                 175
Leu  Asn  Gly  Leu  Ser  Lys  Asp  Lys  Asn  Asp  Asn  Trp  Val  Trp  Ser  Gly
              180                 185                 190
Val  Ser  Phe  Asn  Glu  Phe  Val  Asn  Glu  Lys  Gly  Met  Asp  Lys  Leu  Ser
          195                 200                 205
Cys  Pro  Ile  Tyr  Asp  Ile  Glu  Leu  Glu  Ser  Tyr  Thr  Lys  Lys  Ile  Gln
     210                 215                 220
Glu  Leu  Lys  Phe  Ser  Leu  Phe  Tyr  Arg  Tyr  Ser  Pro  Gly  Arg  Lys  Asn
225                 230                 235                      240
Gln  Val  Ser  Ala  Pro  Thr  Val  Glu  Phe  Ile  Asn  Asn  His  Phe  Ser  Ile
               245                 250                 255
Phe  Ile  Ser  Leu  Pro  Lys  Glu  Ala  Ile  Ala  Ser  Lys  Arg  Lys  Ala  His
              260                 265                 270
Leu  Glu  Ser  Leu  Arg  Gln  Asp  Leu  Pro  Glu  Asp  Leu  Lys  Lys  Ser  Val
          275                 280                 285
Asn  Glu  Gly  Tyr  Leu  Val  Lys  Phe  Lys  Gly  Val  Asp  Leu
     290                 295                 300
```

(2) INFORMATION FOR SEQ ID NO:7:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:7:

```
Met  Glu  Gln  Gln  Xaa  Xaa  Pro  Asn  Pro  Xaa  Ile  Phe  Xaa  Xaa  Ile  Asp
  1                  5                        10                       15
```

( 2 ) INFORMATION FOR SEQ ID NO:8:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:8:

```
Met  Glu  Xaa  Gln  Leu  Xaa  Ser  Ile  Xaa  Xaa  Xaa  Phe  Val  Ala  Asn  Asp
  1                  5                        10                       15
Ile  Asp
```

( 2 ) INFORMATION FOR SEQ ID NO:9:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:9:

```
Met  Glu  Gln  Gln  Lys  Phe  Pro  Asn  Pro  Arg  Ile  Phe  Glu  Asp  Ile  Asp
  1                  5                        10                       15
```

( 2 ) INFORMATION FOR SEQ ID NO:10:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:10:

```
Met  Glu  Arg  Gln  Leu  Lys  Ser  Ile  Ala  Tyr  Ala  Phe  Val  Ala  Asn  Asp
  1                  5                        10                       15
Ile  Asp
```

( 2 ) INFORMATION FOR SEQ ID NO:11:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:11:

```
AGCATCCTCA  TCAATCAAAG  ATACTAC                                            27
```

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

GCTTGAAGAA CAATTCCCTA AGGCATT        27

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

CTGGGAACAA TTCTGAAACA AGATCAG        27

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

ACAGGATCCC TAATTAAAAT TTAAAATTTT AGTAGTTAC        39

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:15:

CATATAGATA AAAATTCAAA GTAC        24

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:16:

AATGTAATTC TTGTGGAAAA AAATATT        27

(2) INFORMATION FOR SEQ ID NO:17:

(i) SEQUENCE CHARACTERISTICS:
        (A) LENGTH: 48 base pairs ( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:17:

AATGGATCCG GAGGTATAAT AATGAATTGG ATATTTAATA CTCTGATT        48

( 2 ) INFORMATION FOR SEQ ID NO:18:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:18:

ACAGGATCCC TAATTAAAAT TTAAAATTTT AGTAGTTAC        39

( 2 ) INFORMATION FOR SEQ ID NO:19:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:19:

AGAGGATCCG GAGGTAATAA AATGGAACGT CAATTAAAAT CAATTGCTTA C        51

( 2 ) INFORMATION FOR SEQ ID NO:20:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:20:

CTAGGATCCT TATTCAGTAA CATTTGGAGG AACGTT        36

( 2 ) INFORMATION FOR SEQ ID NO:21:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:21:

GGAGAGTTAC ATATGGAACA ACAAAAATTC CCTAATCCA        39

( 2 ) INFORMATION FOR SEQ ID NO:22:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: Genomic DNA (  x i  ) SEQUENCE DESCRIPTION: SEQ ID NO:22:

CAAGGATCCA AGCAATTGAT TTTAATTGAC GTTCCA 36

( 2 ) INFORMATION FOR SEQ ID NO:23:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:23:

GGAGAGTTAC ATATGGAACA ACAAAAATTC CCTAATCCA 39

( 2 ) INFORMATION FOR SEQ ID NO:24:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:24:

CTAGGATCCT TATTCAGTAA CATTTGGAGG AACGTT 36

( 2 ) INFORMATION FOR SEQ ID NO:25:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:25:

GGTTGACTTC ATATGGAACG TCAATTAAAA TCAATTGCT 39

( 2 ) INFORMATION FOR SEQ ID NO:26:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:26:

CTAGGATCCT TATTCAGTAA CATTTGGAGG AACGTT 36